United States Patent
Bydlon et al.

(10) Patent No.: US 11,346,730 B2
(45) Date of Patent: May 31, 2022

(54) SYSTEMS AND METHODS FOR DETERMINING THE LENGTH OF A NON-SHAPE-SENSED INTERVENTIONAL DEVICE WITH A SHAPE-SENSED GUIDEWIRE AND DETERMINING A STATE OF THE GUIDEWIRE WITH RESPECT TO AN INTERVENTIONAL DEVICE

(71) Applicant: KONINKLIJKE PHILIPS N.V., Eindhoven (NL)

(72) Inventors: Torre Michelle Bydlon, Melrose, MA (US); Ahmet Ekin, Eindhoven (NL); Paul Thienphrapa, Cambridge, MA (US); Wilhelmus Henrica Gerarda Maria Van Den Boomen, Valkenswaard (NL); Molly Lara Flexman, Melrose, MA (US); Martinus Bernardus Van Der Mark, Best (NL); Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 308 days.

(21) Appl. No.: 16/466,414

(22) PCT Filed: Dec. 1, 2017

(86) PCT No.: PCT/EP2017/081138
§ 371 (c)(1),
(2) Date: Jun. 4, 2019

(87) PCT Pub. No.: WO2018/104162
PCT Pub. Date: Jun. 14, 2018

(65) Prior Publication Data
US 2019/0346319 A1    Nov. 14, 2019

Related U.S. Application Data

(60) Provisional application No. 62/429,907, filed on Dec. 5, 2016.

(51) Int. Cl.
*G01L 1/24*    (2006.01)
*A61B 34/20*    (2016.01)
(Continued)

(52) U.S. Cl.
CPC ............. *G01L 1/242* (2013.01); *A61B 34/20* (2016.02); *G01L 1/246* (2013.01);
(Continued)

(58) Field of Classification Search
CPC ....... G02B 6/02042; G02B 6/34; G01L 1/246; A61B 34/20; A61B 34/35; A61B 5/066;
(Continued)

(56) References Cited

U.S. PATENT DOCUMENTS

2014/0276615 A1*   9/2014   Laroya ................. A61B 8/0891
604/510
2015/0254526 A1   9/2015   Denissen

FOREIGN PATENT DOCUMENTS

WO   2011/141829   11/2011
WO   2013116140   8/2013
(Continued)

*Primary Examiner* — Michael P Mooney

(57) ABSTRACT

A system and method for determining the length of a non-shape-sensed interventional device (102) which includes a shape-sensed guidewire (106) that is received in the lumen (103) of the device. A hub (107) is configured to secure a position of the shape-sensed guidewire and interventional device. A registration module (124) is configured to register a position of the distal tip (117) of the non-shape-sensed interventional device to a position of the shape-sensed guidewire. A determination module (126) determines the length of the non-shape-sensed interventional device using a known position of the device in the hub and the position of the distal tip of the device. The system includes a detection module (146) that receives curvature data from the shape-sensed guidewire and is configured to determine (Continued)

the state of the shape-sensed guidewire with respect to an interventional device.

17 Claims, 18 Drawing Sheets

(51) Int. Cl.
    *G02B 6/02*     (2006.01)
    *A61B 34/35*     (2016.01)

(52) U.S. Cl.
    CPC .......... *G02B 6/02042* (2013.01); *A61B 34/35* (2016.02); *A61B 2034/2061* (2016.02)

(58) Field of Classification Search
    CPC .............. A61B 5/06; A61B 2034/2061; A61B 2090/00; A61B 2090/3966; A61B 2090/067; A61B 2090/376; A61B 2090/061; A61B 2562/0266
    USPC ............................................... 385/12–13, 902
    See application file for complete search history.

(56) References Cited

FOREIGN PATENT DOCUMENTS

| | | |
|---|---|---|
| WO | 2015/049142 | 4/2015 |
| WO | 2015/071343 | 5/2015 |
| WO | 2016/038489 | 3/2016 |
| WO | 2016/041793 | 3/2016 |
| WO | 2016/116796 | 7/2016 |
| WO | 2017055620 | 4/2017 |
| WO | 2018104162 | 6/2018 |

* cited by examiner

SYSTEMS AND METHODS FOR DETERMINING THE LENGTH OF A NON-SHAPE-SENSED INTERVENTIONAL DEVICE WITH A SHAPE-SENSED GUIDEWIRE AND DETERMINING A STATE OF THE GUIDEWIRE WITH RESPECT TO AN INTERVENTIONAL DEVICE

CROSS REFERENCE TO RELATED APPLICATIONS

This application is the U.S. National Phase application under 35 U.S.C. § 371 of International Application No. PCT/EP2017/081138 filed Dec. 1, 2017 published as WO 2018/104162 on Jun. 14, 2018, which claims the benefit of U.S. Provisional Patent Application No. 62/429,907 filed Dec. 5, 2016. These applications are hereby incorporated by reference herein.

BACKGROUND

Technical Field

This disclosure relates to medical instruments and more particularly to systems having shape sensing optical fibers in guidewires for determining a length of a non-shape-sensed interventional device that runs over a shape-sensed guidewire, and determining the state between the guidewire and interventional device.

Description of the Related Art

A medical device may be enabled with shape sensing by embedding an optical fiber(s) within the device. Optical shape sensing (OSS) or Fiber-Optical RealShape™ (hereinafter, "FORS™") employs light along an optical fiber for device localization and navigation during surgical intervention. One principle involved makes use of distributed strain measurements in the optical fiber using characteristic Rayleigh backscatter or controlled grating patterns. Multiple optical fibers can be used together to reconstruct a 3D shape, or a single optical fiber with multiple cores that may also be helixed for a lower-profile sensor. The shape along the optical fiber begins at a specific point along the sensor, known as the launch or z=0, and the subsequent shape position and orientation are relative to that point. FORS™ fibers can be integrated into medical devices to provide live guidance of the devices during minimally invasive procedures.

The inclusion of a FORS™ shape sensing device permits the determination of the shape of the device and a virtual visualization without requiring an imaging device such as an x-ray imaging device. However, the shape sensing device requires customizing the mechanical design of the device to add an additional space for the fiber. Adding the fiber also adds cost to the device and necessitates the use of a shape sensing system. Therefore, to determine the shape of each interventional device a fiber may be added to each device and additional shape sensing systems are required. Alternatively, a hub may be used in connection with a single shape sensed device.

Locking devices such as hubs have been used in connection with shape sensed interventional devices to provide a shape or curvature deformation in the device. The shape of a non-shape-sensed device, such as a catheter that is employed over a guidewire having FORS™ shape sensing, will be defined by the shape of the guidewire for the length over which the devices overlap. The locking device may provide a fixed relationship between the FORS™ guidewire and the catheter.

If the shape-sensed device and non-shape-sensed device are attached to a hub, the starting position may be where the non-shape-sensed device locks onto the hub. However, in order to accurately visualize the non-shape-sensed device as a virtual device, the length and rotation of the non-shape-sensed device with respect to the FORS™ guidewire is needed for a registration step. The length of the device provided by the manufacturer is often inaccurate due to manufacturing variances, etc. However, precise measurements of the length are often required to determine a virtual shape of the non-shape-sensed device. It would be advantageous to register a conventional interventional device that does not have a shape sensing fiber and a shape sensed interventional device that are used with a hub to determine the length and angle of the non-shape-sensed device and accurately visualize the device.

Furthermore, the interaction between a shape-sensed guidewire and an interventional instrument, such as a catheter, may be critical for certain applications. Therefore, it would be advantageous to determine the state of the shape-sensed guidewire with respect to the interventional instrument by monitoring the curvature of the guidewire.

SUMMARY

In accordance with the present principles, a system for determining the length of a non-shape-sensed interventional device is provided. The system includes a non-shape-sensed interventional device having a lumen. The system also includes a shape-sensed guidewire having a shape sensing system that is configured to be received in the lumen of the non-shape-sensed interventional device. A hub is configured to receive the shape-sensed guidewire and the non-shape-sensed interventional device and secure a position of the shape-sensed guidewire and non-shape-sensed interventional device. A registration module is configured to register a position of a distal tip of the non-shape-sensed interventional device to a position of the shape-sensed guidewire. A determination module is configured to determine the length of the non-shape-sensed interventional device using a known position of the non-shape-sensed interventional device in the hub and the position of the distal tip of the non-shape-sensed interventional device.

In another embodiment, a system for determining the length of a non-shape-sensed interventional device is provided. The system includes a non-shape-sensed interventional device having a lumen. The system also includes a shape-sensed guidewire having a shape sensing system that is configured to be received in the lumen of the non-shape-sensed interventional device. A hub is configured to receive the shape-sensed guidewire and the non-shape-sensed interventional device and secure a position of the shape-sensed guidewire and non-shape-sensed interventional device. A determination module is configured to determine the length of the non-shape-sensed interventional device using a known position of the non-shape-sensed interventional device in the hub and a position of the distal tip of the non-shape-sensed interventional device.

In another embodiment, a system for determining a state of a shape-sensed guidewire with respect to an interventional device is provided. The system includes an interventional device having a lumen. The system also includes a shape-sensed guidewire having a shape sensing system that is configured to be received in the lumen of the interventional device. A detection module is configured to receive curvature data from the shape sensing system of the shape-sensed guidewire and determine the state of the shape-sensed guidewire with respect to the interventional device.

In another embodiment, a method for determining the length of a non-shape-sensed interventional device is provided. The method includes the step of securing to a hub a non-shape-sensed interventional device having a lumen and a shape-sensed guidewire having a shape sensing system that is received in the lumen to secure a position of the shape-sensed guidewire and non-shape-sensed interventional device. A position of a distal tip of the non-shape-sensed interventional device is determined. The length of the non-shape-sensed interventional device is determined using a known position of the non-shape-sensed interventional device in the hub and the position of the distal tip of the non-shape-sensed interventional device.

In another embodiment, a method for determining the state of a shape-sensed guidewire with respect to an interventional device is provided. The method includes the step of receiving a shape-sensed guidewire having a shape sensing system in a lumen of an interventional device. Curvature data is acquired from the shape sensing system of the shape-sensed guidewire to determine the state of the shape-sensed guidewire with respect to the interventional device.

In another embodiment, a catheter or other interventional device which can slide freely over a guidewire is combined with a variable mechanical connection which provides a pre-set, but adjustable maximum distance or "swing" for a distal end of the interventional device relative to the guidewire. As in the preceding embodiments, a hub encodes the location of a catheter on a guidewire and enables the visualization of the catheter without x-ray or actively FORS sensing the catheter. In, however, a situation in which the guidewire is further retracted (moved in a proximal direction) from the tip of the catheter, no location information of the catheter would be available from the FORS technology to use for navigation. This situation is detectable with FORS, if one knows the length of the catheter.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
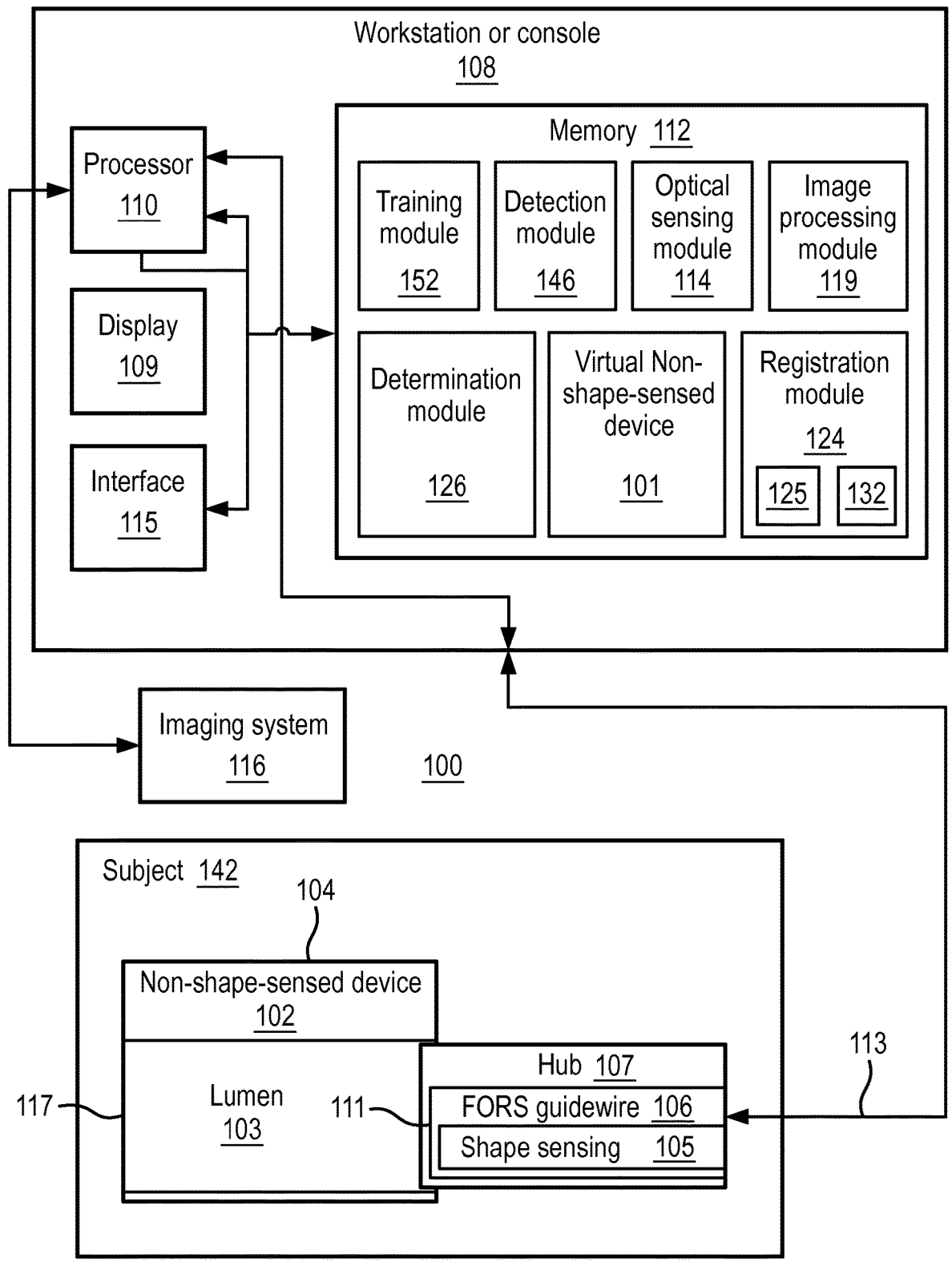
FIG. 1 is a block/flow diagram showing a system for determining the length of a non-shape-sensed interventional device and a state of an interventional device with respect to a FORS™ guidewire in accordance with one embodiment.

In accordance with the present principles, a system for determining the length of a non-shape-sensed interventional device is provided. The system is configured to determine the position of the non-shape-sensed interventional device by utilizing a FORS™ guidewire received in the lumen of the device. The FORS™ guidewire and non-shape-sensed interventional device are preferably secured to a hub. A registration module may be configured to register a position of the distal tip of the non-shape-sensed interventional to a position of the FORS™ guidewire. A determination module is configured to determine the length of the non-shape-sensed interventional device using a known position of the non-shape-sensed interventional device in the hub and the position of the distal tip of the non-shape-sensed interventional device.

The system provides improvements for the visualization of the non-shape-sensed interventional device during an interventional procedure by the generation of a virtual interventional device having the precise length of the interventional device. The system permits the interventional device to be a conventional over the counter device, such as a catheter, which does not require a FORS™ shape sensing system to be incorporated in the device in order for its shape, position and orientation to be tracked and visualized.

The system also includes a detection module which is configured to determine the state of the FORS™ guidewire with respect to an interventional device (either a FORS™ or a non-shape-sensed device). The detection module is configured to receive curvature data from the shape sensing system of the FORS™ guidewire and determine the state of the FORS™ guidewire and interventional device. The system may provide feedback to the user concerning the detected state. The feedback permits a user to restrict the performance of procedures to certain states or to verify the state of the devices. For example, the system may verify that the FORS™ guidewire protrudes from the interventional device in a registration procedure. The status of the FORS™ guidewire protruding from the interventional device may also indicate that the system is in a proper state for visualization by the FORS™ guidewire. The length of the interventional device may also be determined by analyzing the 3D shape position of the guidewire when the state of the FORS™ guidewire indicates that the distal tip of the guidewire is aligned with the distal tip of the interventional device.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems and procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, a system 100 for determining the length of a non-shape-sensed interventional device 102, such as a catheter 104, utilizing a shape-sensed guidewire 106, such as a FORS™ guidewire, is illustratively shown in accordance with one embodiment. While the non-shape-sensed interventional device 102 is illustratively described as being a catheter 104, in other embodiments, the device may be any medical device or instrument that includes a lumen 103 which may receive a guidewire, such as a sheath, a probe, an endograft deployment device, a robot, an electrode, a filter device, a balloon device, a graft, a stent or other medical component. The device that is configured to receive the FORS™ guidewire may be referred to as an "over-the-wire" device.

System 100 may include a workstation or console 108 from which a procedure is supervised and/or managed. Workstation 108 preferably includes one or more processors 110 and memory 112 for storing programs and applications. Memory 112 may store an optical sensing module 114 configured to interpret optical feedback signals from a shape sensing device or FORS™ system 105. The FORS™ guidewire 106 is configured to receive the system 105 therethrough. The optical sensing module 114 is configured to use the optical signal feedback (and any other feedback) to reconstruct deformations, deflections and other changes associated with shape sensed devices.

In a preferred embodiment, the non-shaped sensed interventional device 102 includes a hub 107 that may be configured within the device 102, applied (connected/coupled) to the device 102 or configured to fit within the device 102. The hub 107 is employed to create shape deformation in the FORS™ guidewire 106. In certain embodiments, the hub 107 may include a male Luer lock component at a proximal end of the guidewire lumen in the catheter 104. The Luer lock is used to flush the device with saline prior to use, or to flush with contrast during use. The hub 107 may also have a female Luer lock on its distal portion which can mate onto the proximal end of the catheter 104. This effectively extends the guidewire lumen, and the extended portion is employed to create a known curvature change.

The shape sensing system 105 includes one or more optical fibers which may be arranged in a set pattern or patterns. The optical fibers 113 connect to the workstation 108 through cabling. The cabling may include fiber optics, electrical connections, other instrumentation, etc., as needed.

System 105 with fiber optics may be based on fiber optic Bragg grating sensors, Rayleigh scattering, or other types of scattering. Inherent backscatter in conventional optical fiber can be exploited, such as Raleigh, Raman, Brillouin or fluorescence scattering. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, or in multiple single-core fibers arranged together, the 3D shape and dynamics of the surface of interest can be followed.

A fiber optic Bragg grating (FBG) system may also be employed for system 105. FBG is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

Fresnel reflection at each of the interfaces where the refractive index is changing is measured. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors.

Incorporating three or more cores permits a three dimensional form of such a structure to be precisely determined. From the strain measurement, the curvature of the structure can be inferred at that position. From the multitude of measured positions, the total three-dimensional form is determined. A similar technique can be used for multiple single-core fibers configured in a known structure or geometry.

The workstation 108 includes a display 109 for viewing internal images of a subject 142 or volume. The workstation 108 includes an image processing module 119 that is configured to generate a virtual representation 101 of the non-shape-sensed device as an overlay on medical images such as x-ray images, computed tomography (CT) images, magnetic resonance images (MRI), real-time internal video images or other images as collected by an imaging system 116 in advance or concurrently. Display 109 may also permit a user to interact with the workstation 108 and its components and functions, or any other element within the system 100. This is further facilitated by an interface 115 which may include a keyboard, mouse, a joystick, a haptic device, or any other peripheral or control to permit user feedback from and interaction with the workstation 108.

In a preferred embodiment, as shown in FIG. 1, the system 100 includes a catheter 104 which has a FORS™ guidewire 106 passing therethrough. The catheter 104 and FORS™ guidewire 106 are locked to a hub 107 which includes a Luer lock or other locking mechanism. The system 100 further includes an imaging system 116, such as an x-ray imaging device. The x-ray imaging device is configured to acquire images of the subject 142 in a coordinate system of the x-ray imaging space.

Figure 2:
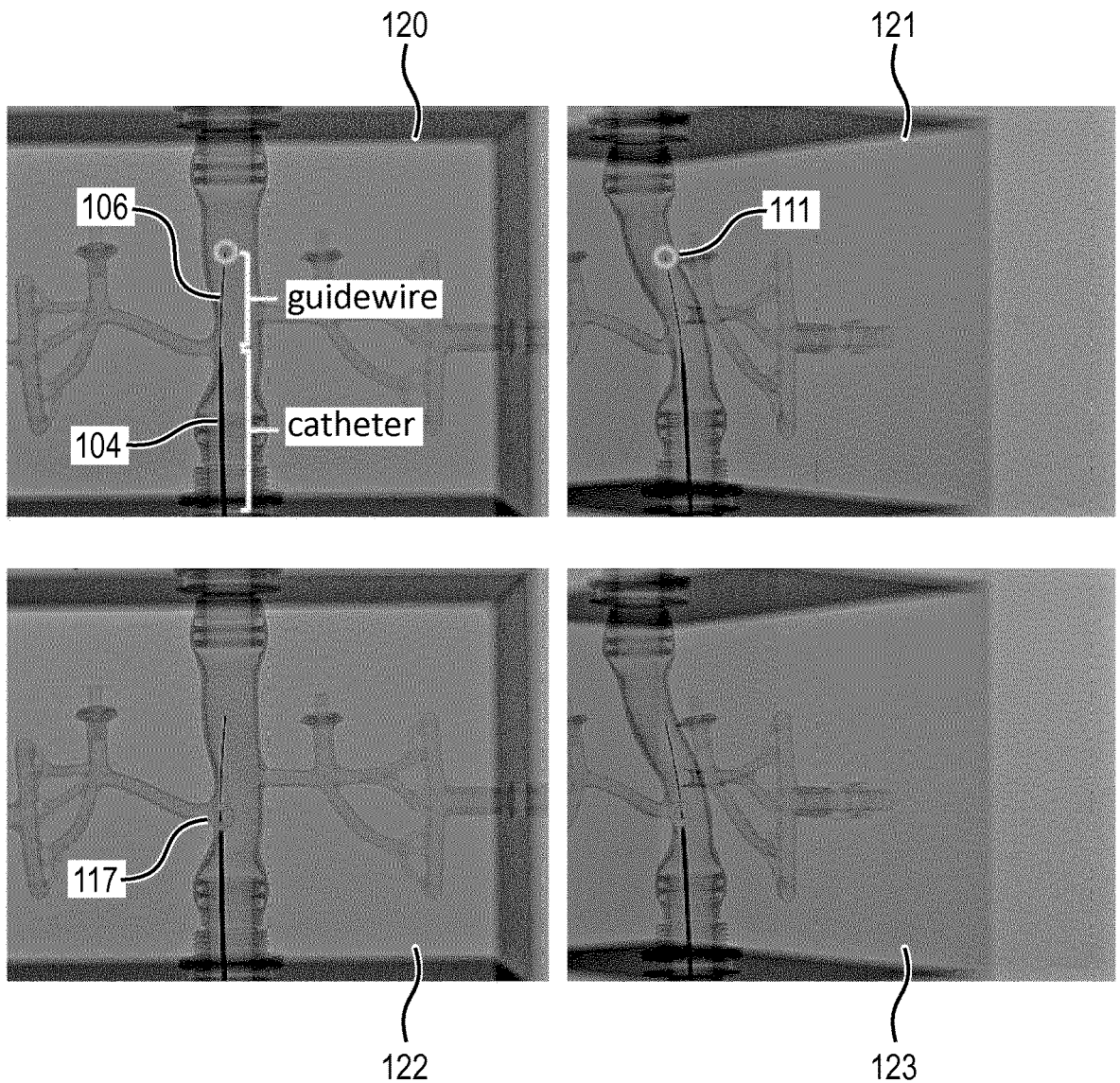
FIG. 2 shows images of a registration procedure performed by the registration module in accordance with one embodiment.

The system 100 includes a registration module 124 which is configured to register the catheter 104 to the FORS™ guidewire 106. In one embodiment, the registration module 124 is configured to receive a selection of the positions of the distal tip 111 of the FORS™ guidewire and the distal tip 117 of the catheter at different angles. As illustratively shown in FIG. 2, in images 120, 121, the distal tip 111 of the guidewire is selected at two different angles to register the FORS™ guidewire 106 to the x-ray imaging space. In images 122, 123, the distal tip 117 of the catheter is selected at two different angles to register the catheter to the x-ray imaging space.

The position of the tips 111, 117 of the FORS™ guidewire and the catheter in the images may be determined manually. For example, the registration module 124 may be configured to receive a command from a user through the interface 115 while viewing the x-ray images on a display 109. Alternatively, the positions of the distal tips 111, 117 of the FORS™ guidewire and catheter may be automatically determined by optical recognition techniques and/or markers as is generally known in the art. For example, to automatically select the catheter tip 117, the catheter 104 may be moved to two or more positions and imaged by the imaging system 116. Optical recognition techniques such as a search algorithm may be employed as is generally known in the art, to locate the catheter tip 117 and/or FORS™ guidewire tip 111.

A determination module 126 is configured to receive the position of the FORS™ guidewire tip 111 as well as the position of the start of the FORS™ guidewire and catheter based on their securement to the hub 107 at a known position in the x-ray coordinate space. The determination module 126 is configured to determine the position of the catheter tip 117 relative to the hub position using the x-ray coordinates and determine the length of the catheter in order to provide an improved visualization of a virtual catheter during an interventional procedure.

Figure 3:
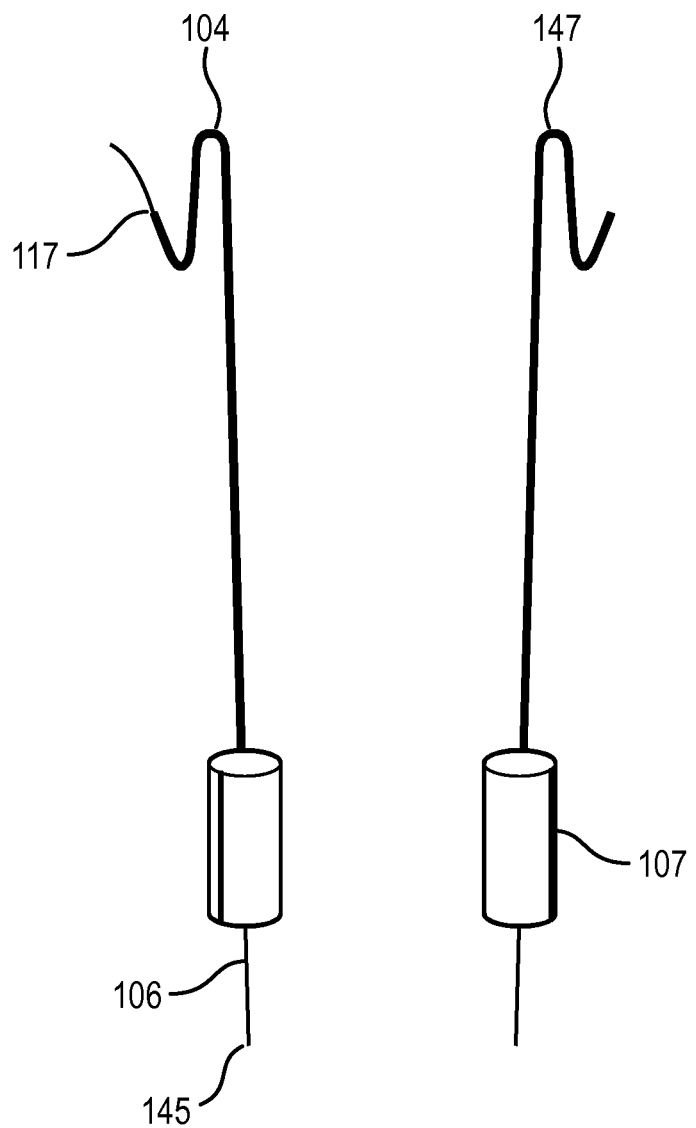
FIG. 3 shows images of a registration procedure for the hub rotation angle performed by the registration module in accordance with one embodiment.

The system 100 is also configured to determine rotation of the hub 107. The registration module 124 is configured to register an initial angle of the hub 107. For example, as shown in image 145 of FIG. 3, the imaging system 116, such as an x-ray imaging device, is configured to acquire an image of the hub 107, catheter 104 and/or FORS™ guidewire 106 at a first position. The angle of the hub 107 at the first position is initialized to 0 and this position is stored by the registration module 124. The imaging system 116 is configured to acquire additional images of the hub 107, catheter 104 and/or FORS™ guidewire 106 as the hub is rotated during an interventional procedure. For example, image 147 of FIG. 3, shows the hub 107, catheter 104 and FORS™ guidewire 106 after they have been rotated. The determination module 126 is configured to compare the current angle of the hub 107 with the initial angle of the hub to determine an angular rotation of the hub. In a preferred embodiment, the hub has a unique shape or a marker which allows the current angle to be easily determined with respect to the initial angle in images acquired by the imaging system 116.

Since the FORS™ guidewire 106 and the catheter 104 are both secured to the hub 107, any rotation of the hub will cause a corresponding rotation of the catheter. As shown in FIG. 3, the catheter 104 may include a distinctively shaped distal tip 117. The registration module 124 is preferably configured to register a shape and orientation of the distal tip 117 of the catheter with the initial angle of rotation of the hub 107. The distal tip 117 of the catheter is preferably in a non-foreshortened configuration during the initial registration to increase the accuracy of the registration. Furthermore, the catheter 104 preferably has a degree of torsional stiffness.

The determination module 126 is configured to utilize the comparison of the current angle of the hub 107 with the initial angle of the hub to determine the shape and orientation of the distal tip 117 of the catheter. This permits the system 100 to provide an accurate virtual representation 101 of the non-shape-sensed device even in situations where there is no shape information concerning the tip of the catheter, such as when the FORS™ guidewire 106 is pulled back inside the lumen 103 of the catheter. In alternative embodiments, the determination module 126 is configured to acquire the current orientation and shape of the distal tip 117 of the catheter in an image acquired by the imaging system 116 and determine the angle of rotation of the hub by comparing the current orientation and shape of the distal tip of the catheter with the registered shape and orientation of the distal tip of the catheter at the initial angle of rotation of the hub.

Figure 4:
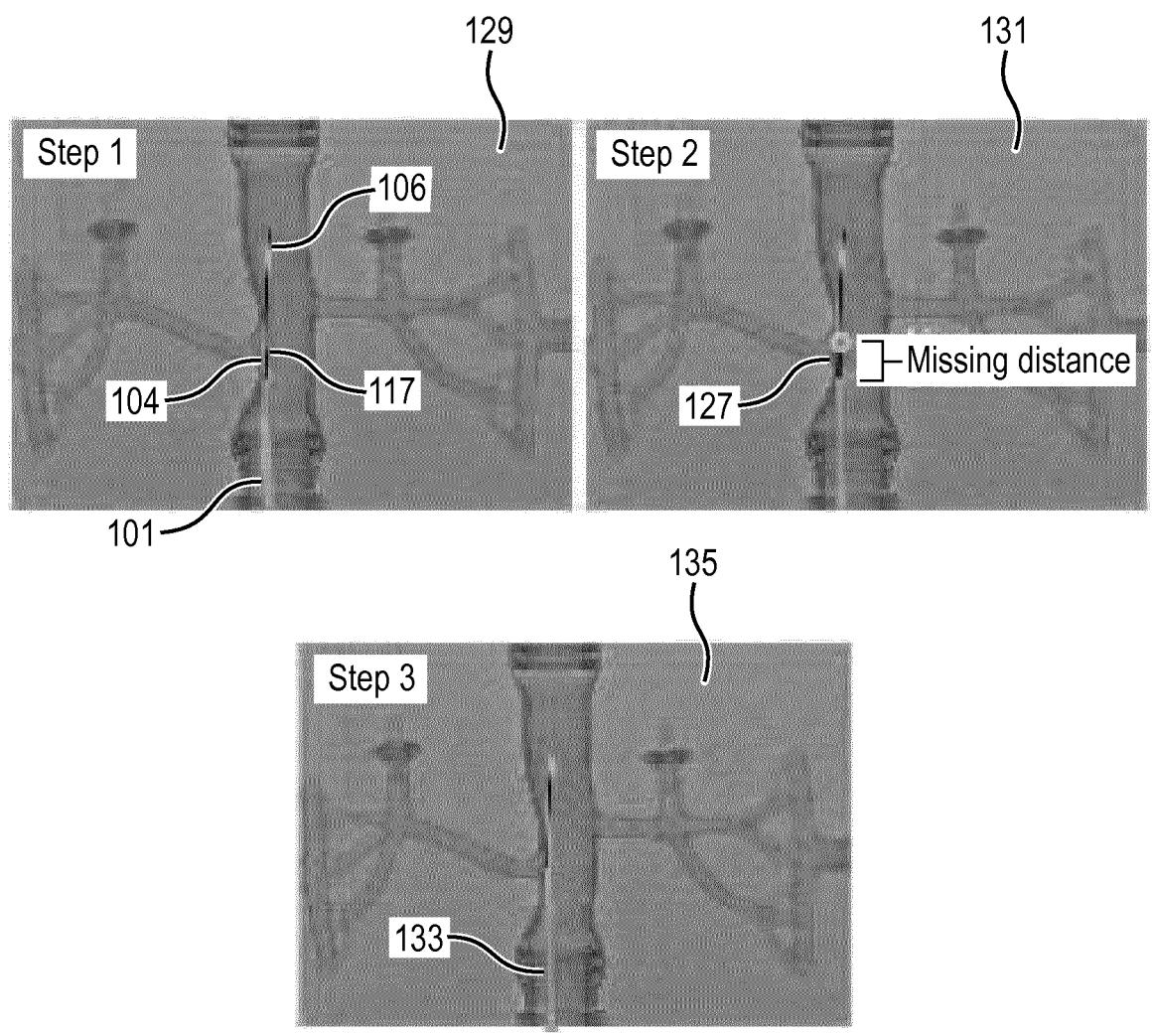
FIG. 4 shows images of the determination of the length of a non-shape-sensed interventional device in accordance with one embodiment.

Alternatively, as shown in FIG. 4, the system 100 may be configured to determine the length of the catheter 104 without an explicit registration of the catheter to the x-ray imaging space. In this embodiment, the registration module 124 is configured to store a predetermined length 125 of the catheter, such as the length set by the manufacturer for the device. As shown in image 129, the system 100 is configured to generate a virtual catheter 101 utilizing the location of the hub 107 as the starting point and the predetermined length. The virtual catheter 101 is superimposed over an image of the catheter 104 acquired by the imaging system 116. The actual catheter tip 117 in the image is selected manually or automatically.

As shown in image 131, the length of the virtual catheter 101 differs from the actual length of the catheter shown in the image. The determination module 126 is configured to determine the length of the catheter 104 by calculating the difference 127 between the tip of the virtual catheter and the actual position of the catheter tip 117 selected in the x-ray image. As shown in image 135, the system 100 is then configured to generate an updated virtual catheter 133 in accordance with the length determined by the determination module 126.

In another embodiment, system 100 is configured to determine the length of the catheter 104 by registering a position of the distal tip 117 of the catheter when it is aligned with the distal tip 111 of the FORS™ guidewire. In this embodiment, the catheter tip 117 and the FORS™ guidewire tip 111 are aligned while having the catheter 104 and FORS™ guidewire 106 locked to the hub 107. The registration module 124 is configured to designate the known position of the hub 107 as the start of the catheter 104. The registration module 124 is configured to designate the position of the distal tip 111 of the FORS™ guidewire determined by the FORS™ system 105 as the ending position of the catheter 104. The determination module 126 is configured to receive the positions and calculate the difference between the distal tip 111 of the FORS™ guidewire and the known position of the hub 107 to determine the length of the catheter 104. In a preferred embodiment, smart clips are clamped over the catheter 104 and the FORS™ guidewire 106 to bend both devices at the same place and in the same direction for improved calibration.

Figure 5:
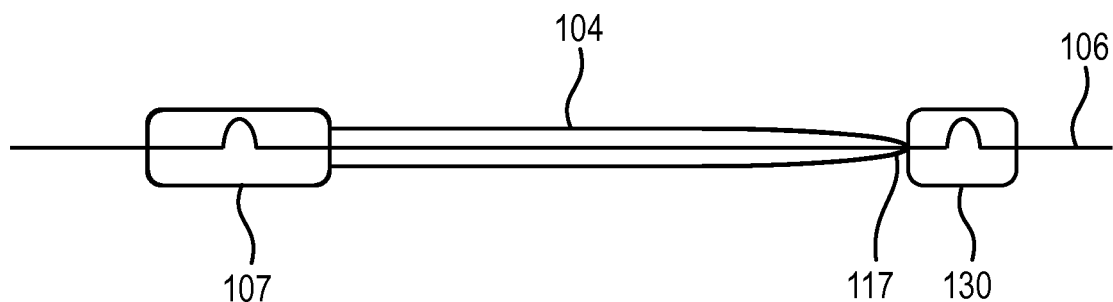
FIG. 5 shows images of the system featuring a tip hub in accordance with one embodiment.

In another embodiment shown in FIG. 5, the system includes a tip hub 130 that is configured to interact with the distal tip 117 of the catheter to secure the catheter tip at a known position. In a preferred embodiment shown in FIG. 5, the tip hub 130 is configured so that the distal end of the catheter 104 is secured to the tip hub 130 in a known, repeatable manner. For example, the lumen of the tip hub 130 may have dimensions which permit the FORS™ guidewire 106 to pass through the lumen but are too narrow to permit the catheter 104 to pass therethrough. In this embodiment, the distal tip 117 of the catheter is secured flush against the hub. The determination module 126 is configured to subtract the known position of the hub 107 and tip hub 130 to determine the length of the catheter 104.

The tip hub 130 may also be configured to shape the FORS™ guidewire 106 in a specific manner which automatically triggers registration, such as based on a software configured to trigger the registration module 124 to perform registration upon recognizing a specific shape. In other embodiments, the shape of the FORS™ guidewire 106 within the tip hub 130 is uniquely identifiable. The uniquely identifiable shape allows registration to be performed automatically using a minimum length recorded.

The tip hub 130 is preferably temporarily installed during the registration step to determine the length of the catheter 104 and is removed after the registration step. The tip hub 130 may be temporarily secured via a clip, clamp, by hand or other methods known in the art.

The registration module 124 may utilize the position and initial rotational information of the FORS™ guidewire 106 in the hub 107 to correct for twisting or rotation of the catheter 104 as it extends from the hub to the tip hub 130. For example, the extent of mismatch between the rotational angles of the proximal and distal ends of the catheter 104 may be determined to correct the virtual catheter or for calibration purposes.

In a preferred embodiment, the registration module 124 is configured to subtract the rotation angles of the device at the tip hub 130 from the initial position and rotational angle. The registration module 124 may include a look-up table 132 which utilizes the initial rotational information of the FORS™ guidewire 106 in the hub 107 to correct for twisting or rotation of the catheter 104 in the registration.

Figure 6:
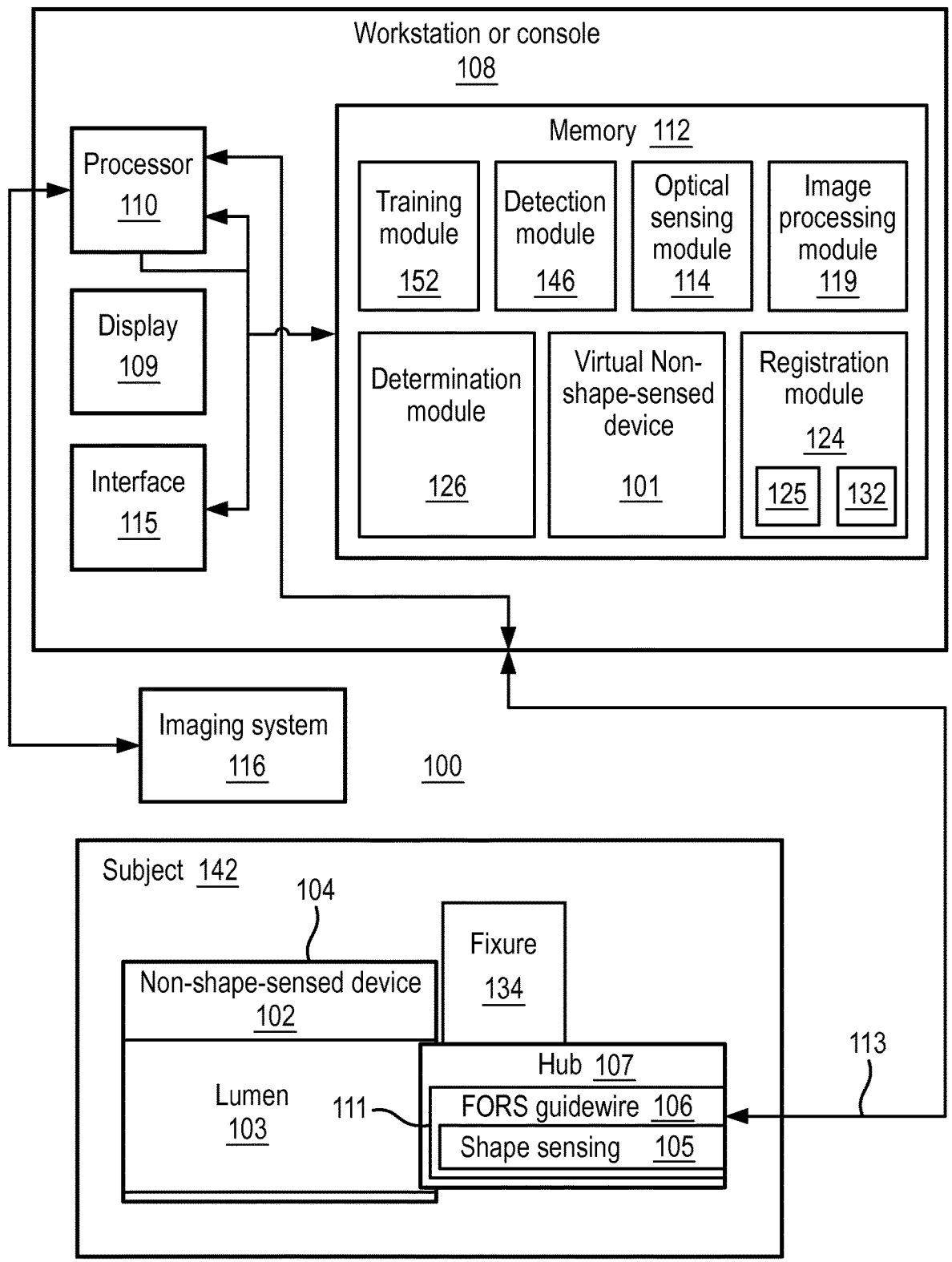
FIG. 6 is a block/flow diagram showing a system for determining the length of a non-shape-sensed interventional device and a state of an interventional device with respect to a FORS™ guidewire featuring a fixture in accordance with one embodiment.

In another embodiment shown in FIG. 6, the system 100 includes a fixture 134 which is configured to receive a portion of the catheter tip 117 which is looped back onto the fixture from the hub 107. The registration module 124 is configured to register the catheter 104 using the known position of the fixture 134 in x-ray imaging space. In a preferred embodiment, the fixture 134 is fixed to a proximal segment of the FORS™ guidewire 106.

Alternatively, the user may loop the catheter tip 117 back to the FORS™ guidewire 106 and hold the catheter tip in that position without the use of a fixture 134. In this embodiment, the registration module 124 is configured to determine the position of the catheter tip 117 by locating a crossover point as the closest two points of the sensor.

In another embodiment, the system may include a second FORS™ guidewire. A second hub is configured to receive the second FORS™ guidewire and fix its position. The second hub is also configured to receive the catheter tip 117 which extends from the hub 107. The position of the catheter tip 117 is measured by the second FORS™ guidewire and the registration module 124 is configured to register the catheter tip using the position of the catheter tip. Alternatively, the catheter tip 117 may be placed by the user in contact with a second FORS™ device that is not a guidewire.

In alternative embodiments, the catheter tip 117 may be determined by another localization device or procedure that is registered to the shape sensing system 105. For example, the localization device or procedure may include a fixed point in space, a mechanical fixture, EM tracking, optical tracking, image-based tracking, etc. The localizer device or procedure provides determination of the position of the catheter tip 117. The determination module 126 is configured to utilize the position of the catheter tip 117 determined by the registration module 124 and the known position of the beginning point of the catheter in the catheter hub to determine the length of the catheter 104 or other non-shape-sensed device 102.

Figure 7:
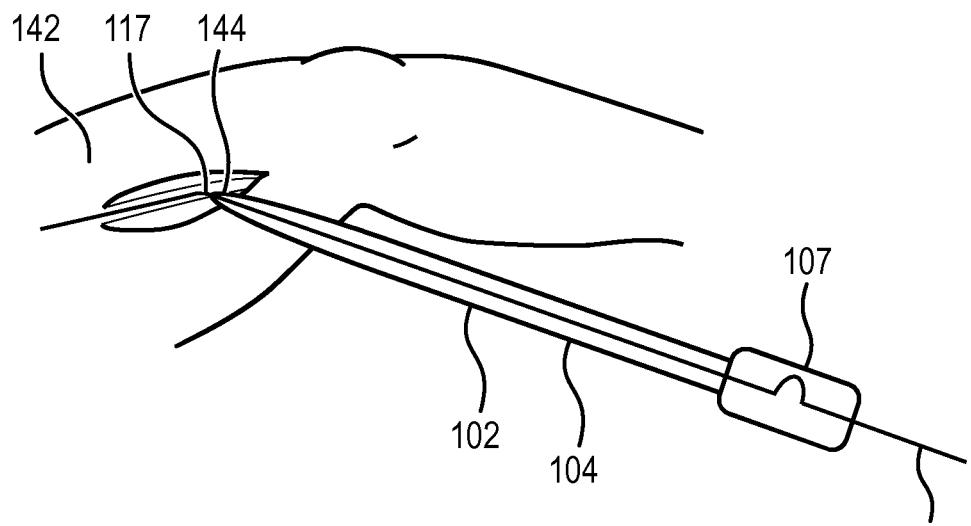
FIG. 7 shows images of a registration procedure performed by the registration module with the non-shape-sensed interventional device positioned at a body insertion point in accordance with one embodiment.

In another embodiment shown in FIG. 7, the FORS™ guidewire 106 and the non-shape-sensed device 102, such as a catheter 104, are configured to extend from the hub 107 towards an internal region of the subject 142 with the tip of the non-shaped sensed device, such as a catheter tip 117, positioned at the body insertion point 144, and the FORS™ guidewire 106 inside the subject. The shape sensing system 105 of the FORS™ guidewire 106 is configured to measure temperature-induced strain to determine the transition point between the interior of the subject 142 and the exterior of the subject. The registration module 124 is configured to register the transition point as the distal tip of the non-shape-sensed device 102. The beginning point of the non-shape-sensed device 102 is the hub 107. The determination module 126 is configured to receive the positions of the proximal and distal ends of the non-shape-sensed device and determine the length of the device.

Figure 8:
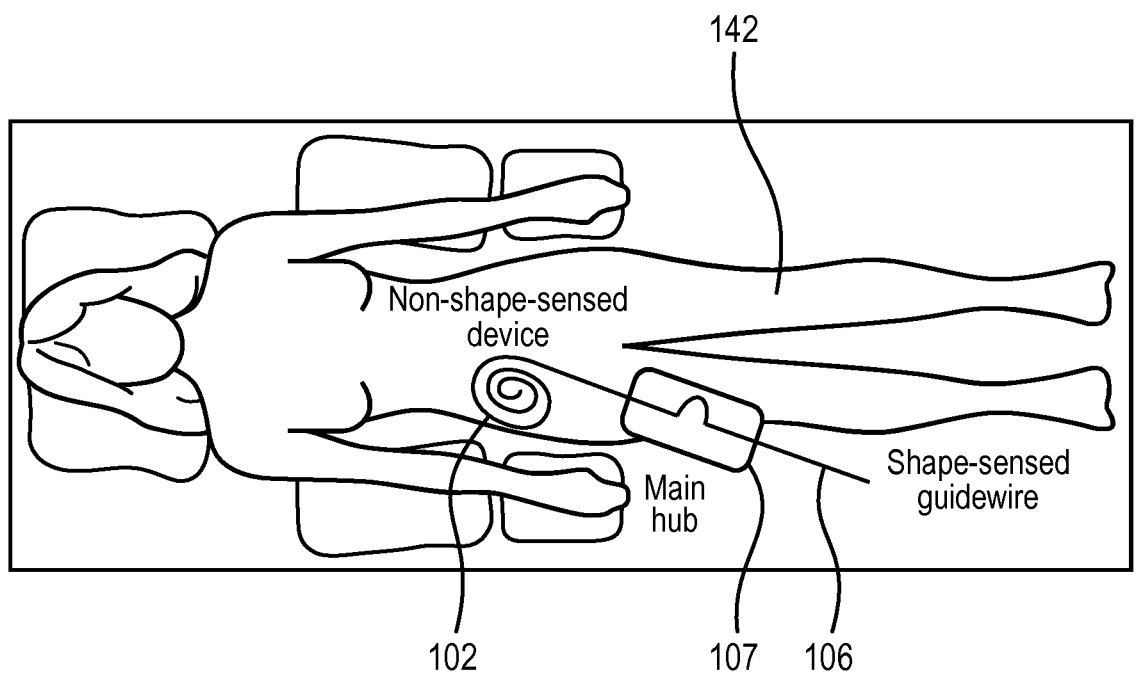
FIG. 8 shows images of the determination of the length of a non-shape-sensed interventional device in accordance with another illustrative embodiment.

In another embodiment shown in FIG. 8, the imaging system 116, such as an x-ray imaging system, is configured to image the entire non-shape-sensed device 102 in a field of view. For example, the non-shape-sensed device 102 may be coiled or folded in a manner that avoids overlap with itself. The position of the non-shape-sensed device 102 may then be obtained in x-ray imaging coordinates. The determination module 126 is configured to determine the length of the non-shape-sensed device 102 based on the positions of the body of the non-shape-sensed device in the image. The determination module 126 is also configured to utilize the rotation angle of the hub to determine the length of the non-shape-sensed device based on registration of the initial rotation angle, as previously described.

Figure 9:
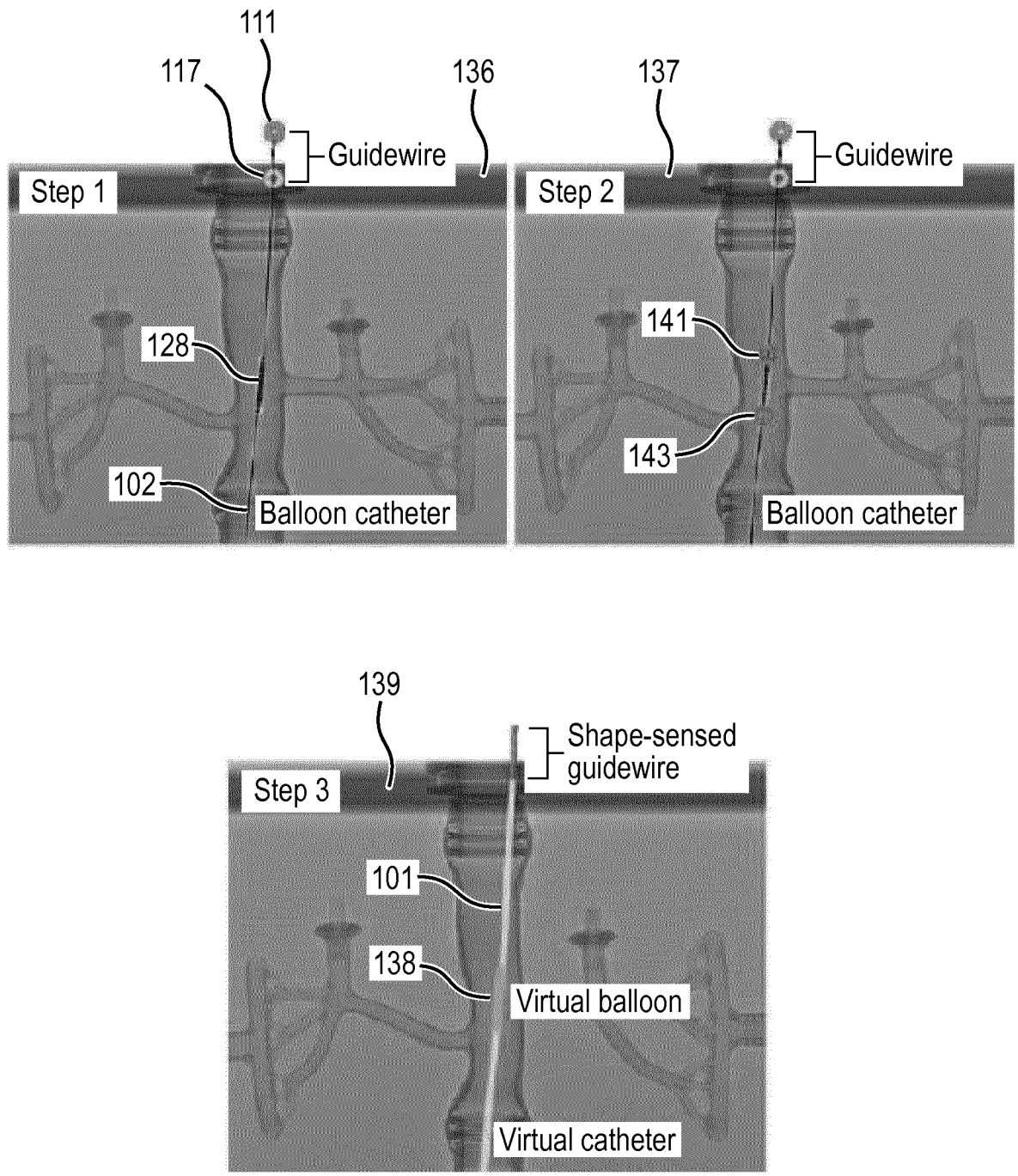
FIG. 9 shows images of the determination of the positions of a catheter and interventional tool which is positioned on the catheter, and the generation of a virtual catheter and virtual interventional tool in accordance with one embodiment.

As shown in FIG. 9, in a further embodiment, the determination module 126 is configured to determine the location that an interventional tool 128, such as a balloon, stent, graft, is located along the non-shape-sensed device 102. In this embodiment, the interventional tool 128 may include radiopaque markers to help identify the interventional tool in an image, such as an x-ray image. As shown in image 136, the determination module 126 is configured to receive a selection of the tip 111 of the FORS™ guidewire and the tip 117 of the catheter, either manually or automatically, in the x-ray image. As shown in image 137, the determination module 126 is also configured to receive a selection of the position of the first and second ends 141, 143 of the interventional tool 128 which may be selected either manually or automatically in the x-ray image. As shown in image 139, the determination module 126 is configured to receive the position of the ends 141, 143 of the interventional tool 128 and the image processing module 119 is configured to provide a visualization 138 of the interventional tool along with the virtual catheter 101.

Figure 10:
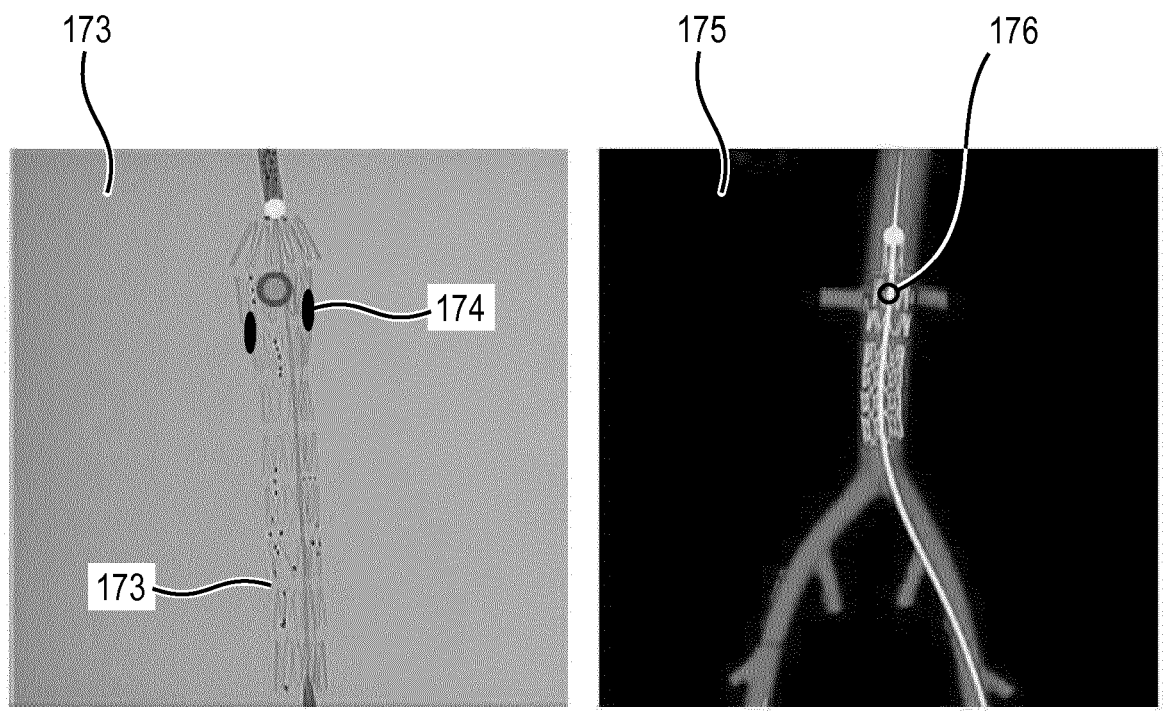
FIG. 10 shows images of the generation of a virtual representation of an endograft having radiopaque markers based on the hub rotation angle in accordance with one embodiment.

As shown in FIG. 10, in other embodiments, the determination module 126 is configured to determine the location of an interventional tool having increased complexity, such as a fenestrated endograft 172, utilizing numerous radiopaque markers based on the determined rotation of the hub 107. As shown in image 173 of FIG. 10, the fenestrated endograft 172 has several radiopaque markers 174 which help the physician orient the graft once inside the body. The registration module 124 may be configured to receive a selection by the user of the position of at least one of the radiopaque markers 174 in an image when the hub 107 is at an initial rotation angle. As shown in image 175 of FIG. 10, the radiopaque markers 174 may be color coded with respect to the initial rotational angle of the hub/interventional tool handle and displayed as part of the virtual representation 176 of the endograft. When the hub 107 is rotated, the determination module 126 is configured to determine the rotation of the hub. The image processing module 119 is configured to rotate the color-coded radiopaque markers 174 on the virtual representation an amount corresponding to the rotation of the hub. The system is configured provide the virtual representation of the endograft and the radiopaque markers in non-deployed, semi-deployed, and fully deployed states of the interventional tool.

The system 100 also includes a detection module 146 that is configured to receive curvature data from the shape sensing system 105 concerning the tip 111 of the FORS™ guidewire to determine the relationship between the FORS™ guidewire 106 and the non-shape-sensing device 102, such as the catheter 104. For example, during an interventional procedure the relationship of the tip 111 of the FORS™ guidewire and the tip 117 of the catheter may have three general states: the guidewire tip may be protruding from the catheter, the guidewire tip may be inside the catheter or the catheter tip and the guidewire tip are aligned. The determination of one of these states by the detection module 146 is advantageous for determining whether shape registration should be performed and the appropriate image processing procedure for such registration. The determination that the tips 111, 117 are aligned may also permit determination of the length of the catheter 104 or other non-shape-sensed device 102.

The system 100 is configured to determine a maximum curvature of the FORS™ guidewire tip in a default position when there are no forces applied on the FORS™ guidewire tip and the shape of the tip is in its default form. In one embodiment, the tip 111 of the FORS™ guidewire is released for a relatively short period of time and the detection module 146 is configured to receive the shape information concerning the FORS™ guidewire 106 from the shape sensing system 105 and calculate a maximum curvature at the tip 111 of the FORS™ guidewire for various incoming shapes and a range of the maximum curvature of the guidewire tip. The maximum curvature estimates are stored in the detection module 146. Alternatively, the maximum curvature may be measured during an initial device calibration step and stored in the detection module 146.

The FORS™ guidewire 106 is configured to measure its curvature during a training phase wherein the guidewire is moved through a catheter lumen at numerous different positions with respect to the catheter lumen 103. The detection module 146 is configured to collect the curvature data concerning the FORS™ guidewire from the shape sensing system 105 during the training phase.

In a preferred embodiment, the system 100 may include a training module 152 which is configured to provide instructions to the user concerning the movements for the FORS™ guidewire 106 required for the training stage so that a sufficient number of data points are collected and the data points are associated with each of the three states. The training module 152 may be configured to provide the instructions on the display 109 or through other feedback such as audio or haptic feedback. For example, the training module 152 may be configured to instruct the user to place the FORS™ guidewire 106 in various positions while inside the catheter 104, protruding from the catheter and aligned with the catheter. In an alternative embodiment, a robot is utilized to manipulate the FORS™ guidewire with respect to the catheter 104 to acquire a large amount of curvature data.

The collection of a large amount of data in the training phase may permit the detection module 146 to apply sophisticated algorithms, such as deep learning to determine the curvature data and its parameters. In some embodiments, a statistical learning approach may be implemented on the training data.

As shown in FIGS. 11-14, the detection module 146 is configured to receive the curvature data from the shape sensing system 105 and plot the curvature data as a graph 148. The detection module 146 is configured to analyze peaks 149 in the graph and the training data to determine the state of the FORS™ guidewire 106 with respect to the catheter 104 or other non-shape-sensed device 102. For example, FIGS. 11-14 show curvature data for the FORS™ guidewire 106 as it progresses from protruding from the catheter to its distal tip 111 being aligned with the distal tip 117 of the catheter.

Figure 11:
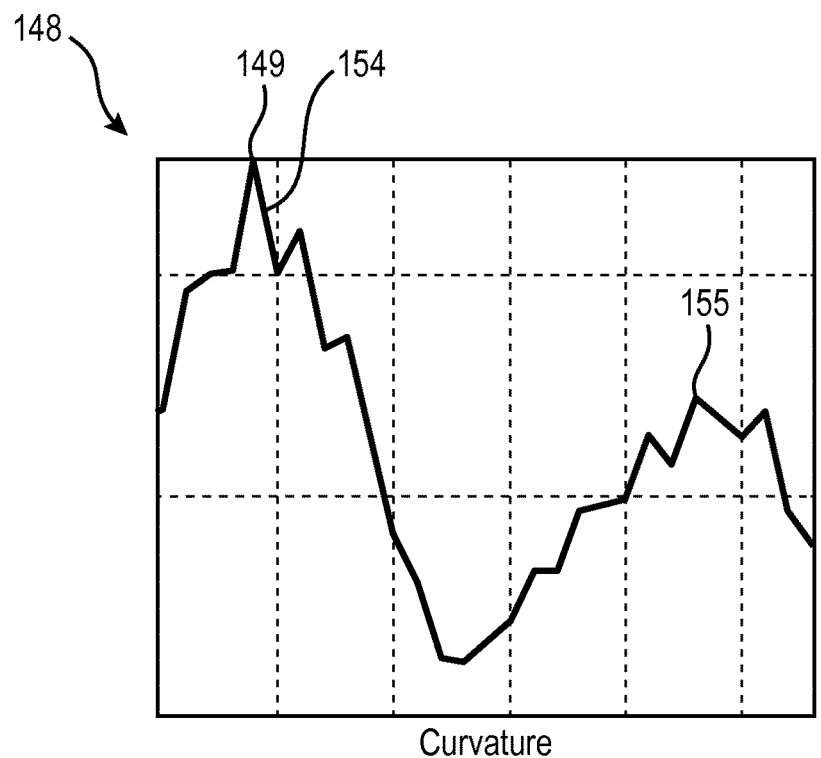
FIG. 11 is a graph showing curvature data received by the detection module having two peaks.
Figure 12:
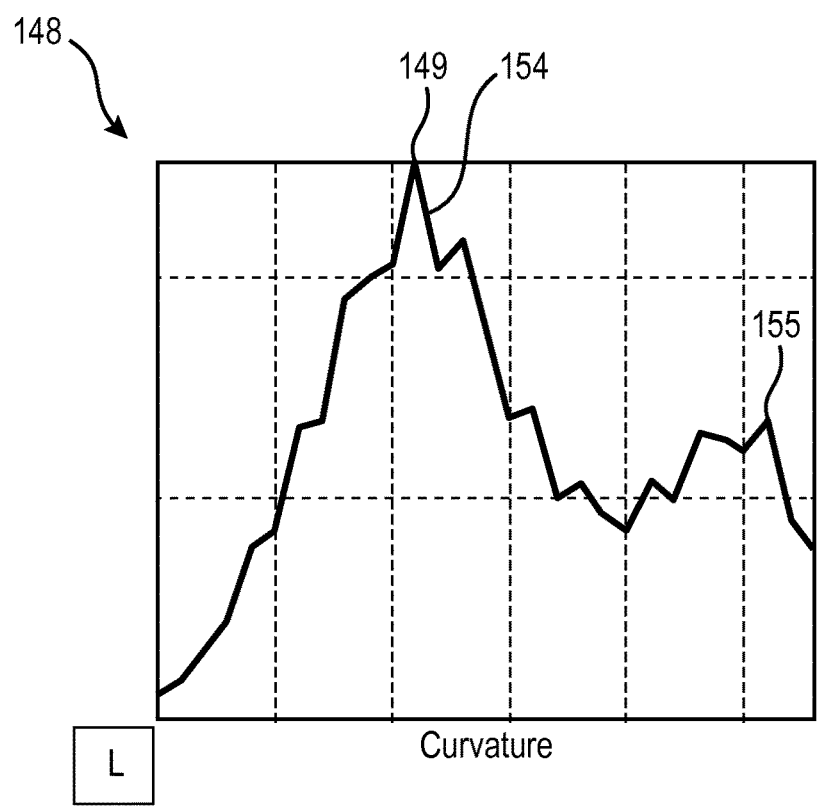
FIG. 12 is a graph showing curvature data received by the detection module having two peaks.
Figure 13:
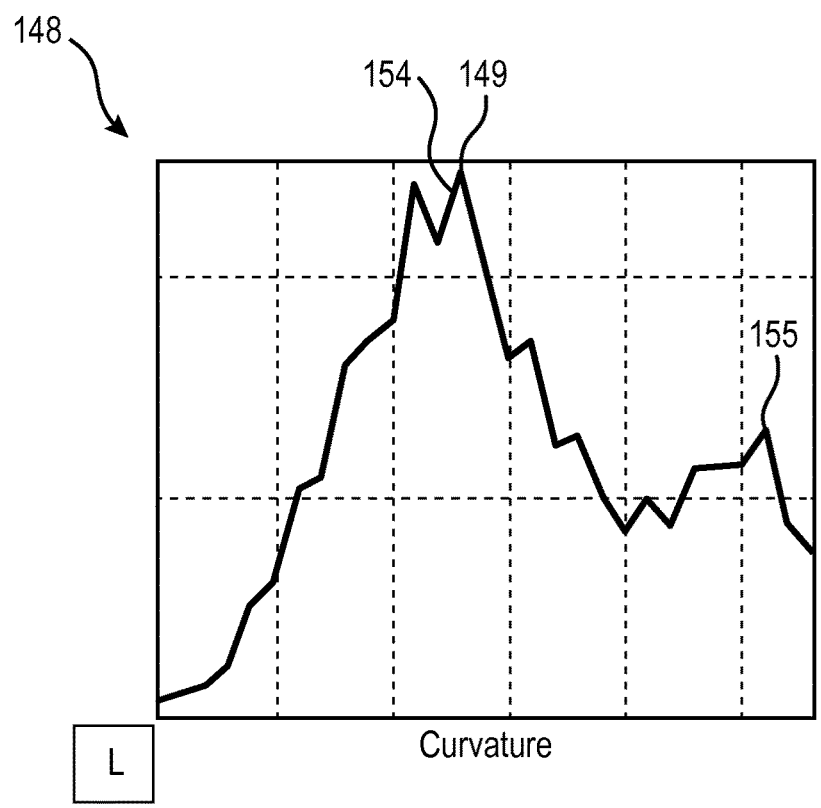
FIG. 13 is a graph showing curvature data received by the detection module having two peaks.

In the curvature data shown in FIGS. 11-13, the first peak 154 has a magnitude of approximately 125 and the training data indicates that the catheter 104 is bent. The second peak 155 in FIGS. 11-13 has a smaller magnitude that it is more distally located. The training data indicates that this curvature data is associated with the FORS™ guidewire tip 111 being in a state where it is protruding from the catheter 104.

Figure 14:
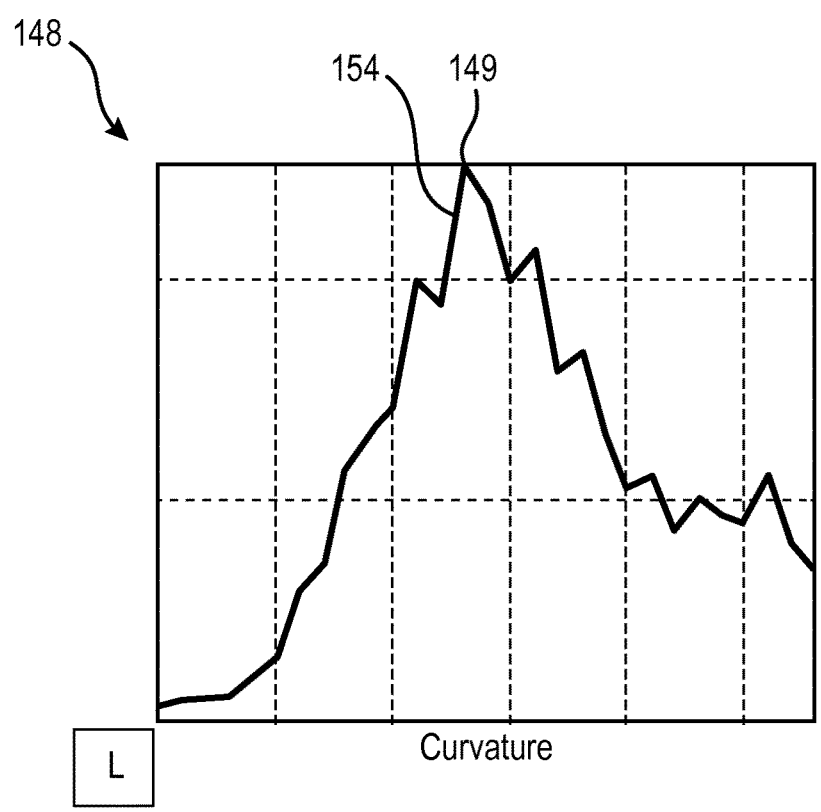
FIG. 14 is a graph showing curvature data received by the detection module having one peak.
Figure 15:
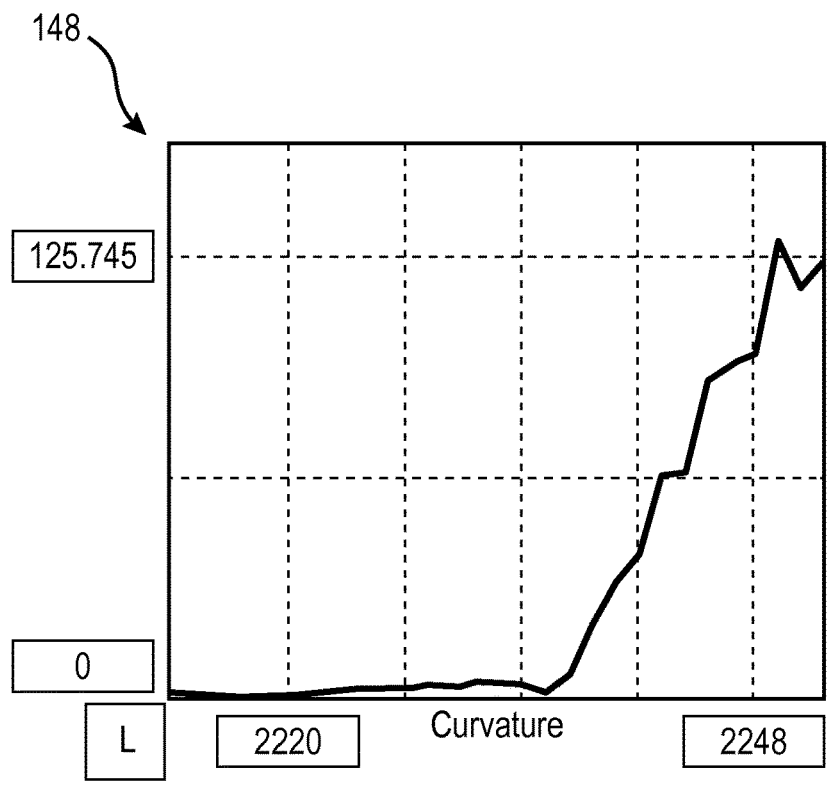
FIG. 15 is a graph showing curvature data received by the detection module.
Figure 16:
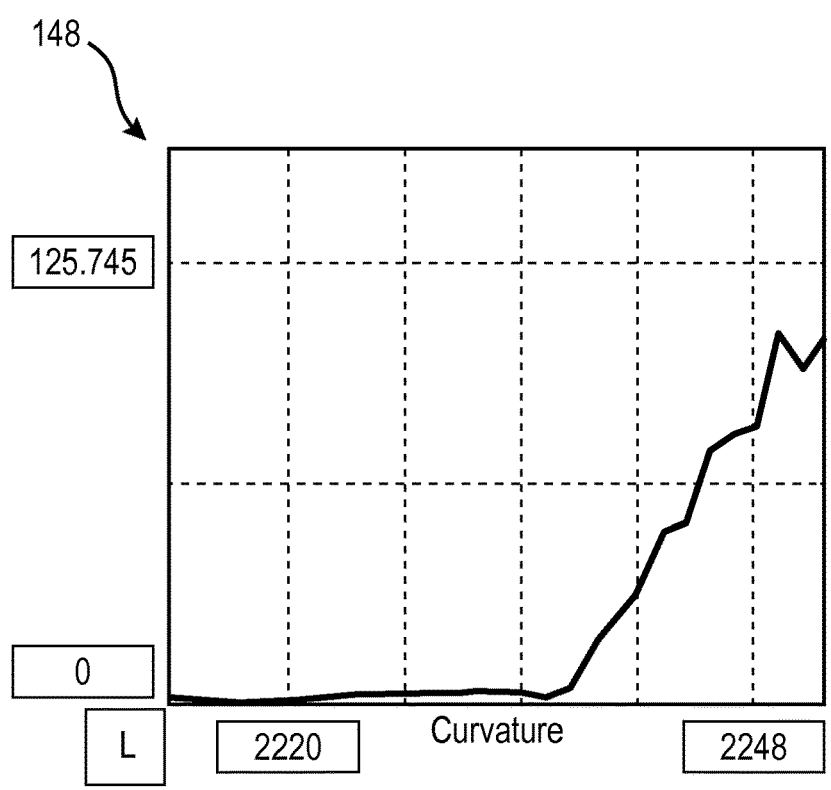
FIG. 16 is a graph showing curvature data received by the detection module.
Figure 17:
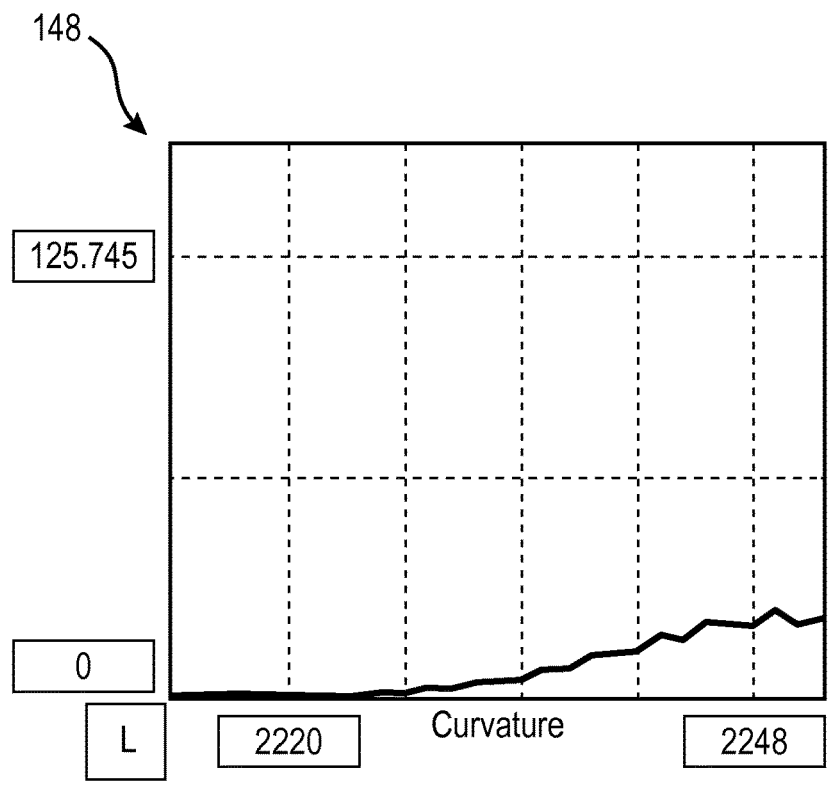
FIG. 17 is a graph showing curvature data received by the detection module.
Figure 18:
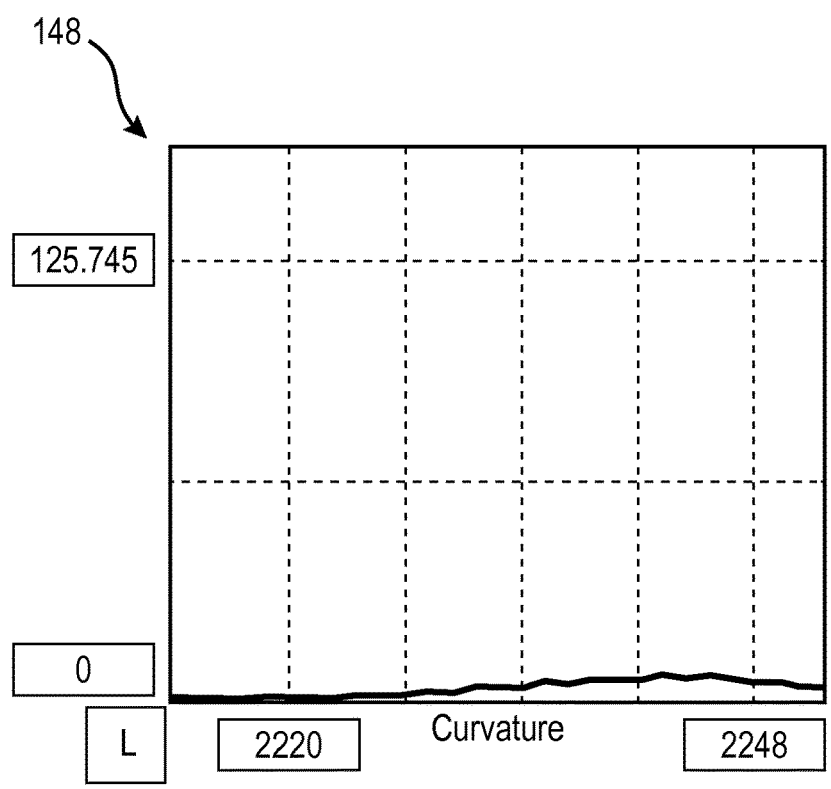
FIG. 18 is a graph showing curvature data received by the detection module.

The detection module 146 is configured to determine that FORS™ guidewire tip 111 is protruding from the catheter 104 when there are two peaks visible based on the training data. The detection module 146 is configured to determine that the tips 111, 117 of the FORS™ guidewire and the catheter are aligned when there is only one peak as shown in FIG. 14. FIGS. 15-18 show curvature data as the FORS™ guidewire 106 is being pulled back further inside the catheter 104. The curvature data in FIG. 15 has a raised curvature on the rightmost side of the curvature plot indicating that the FORS™ guidewire 106 is just inside the catheter 104. The raised curvature decreases in FIGS. 16-17 until it no longer exists in FIG. 18. The curvature plot in FIG. 17 indicates that the FORS™ guidewire 106 is farther inside the catheter 104.

Figure 19:
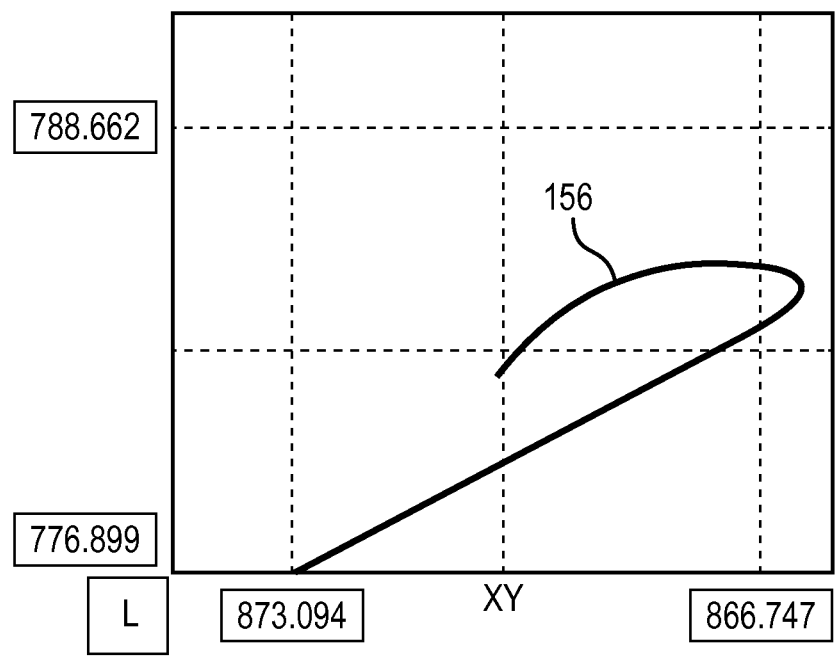
FIG. 19 is a graph showing an interventional device in an (x,y) plane whose 2D curvature data having two peaks received by the detection module.
Figure 20:
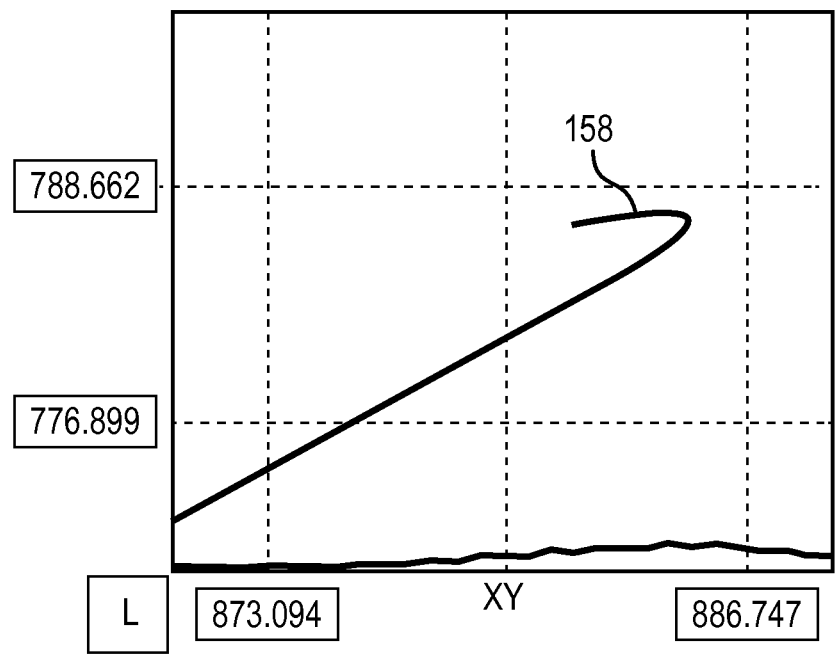
FIG. 20 is a graph showing an interventional device in an (x,y) plane whose 2D curvature data having a single peak received by the detection module.
Figure 21:
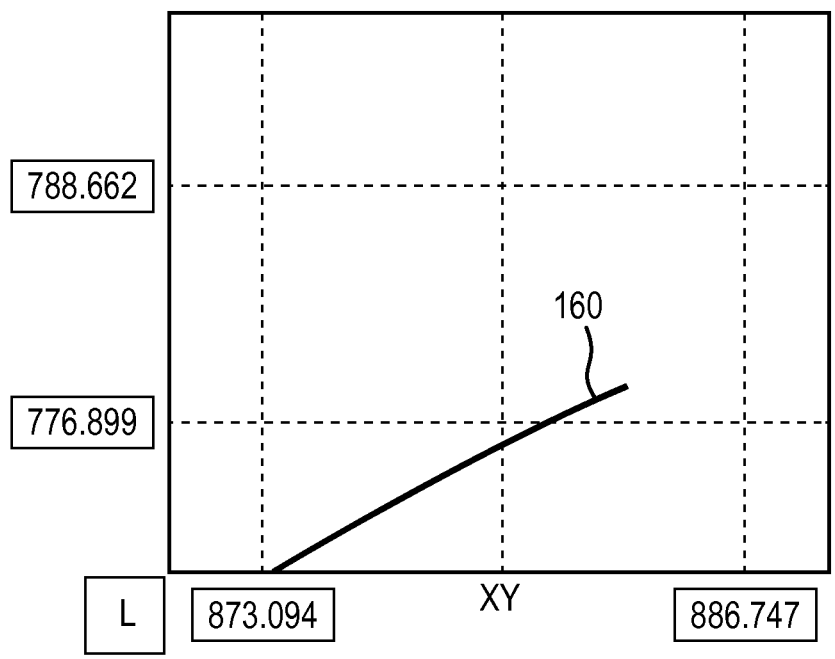
FIG. 21 is a graph showing an interventional device in an (x,y) plane whose 2D curvature data having no peak received by the detection module.

In an alternative embodiment shown in FIGS. 19-21, the detection module is configured to project the shape sensing data from the FORS™ guidewire 106 onto an x, y, z plane and determine 2D curvature to determine the state of the FORS™ guidewire 106 and catheter 104. For example, the specific (x,y) projection 156 shown in FIG. 19 indicates that the guidewire tip 111 is protruding out of the catheter 104 when there are two peaks in the curvature data. The specific (x,y) projection 158 shown in FIG. 20 indicates that the tips 111, 117 of the FORS™ guidewire and catheter are aligned with one peak in the curvature data. The specific (x,y) projection 160 shown in FIG. 21 indicates that the FORS™ guidewire 106 is inside the catheter 104 with no peak in the curvature data. The 2D curvature data computed at the aforementioned positions is useful for identifying the transition between the states. The 2D curvature may be used by the detection module 146 in combination with the 3D curvature data or by itself.

In one embodiment, the detection module 146 is configured to analyze the maximum curvature and compare the curvature to the training data acquired during the training phase. When the maximum curvature detected by the detection module 146 is below a threshold value determined from the training data, the detection module is configured to determine that the FORS™ guidewire tip 111 is inside the catheter 104 and the catheter tip 117 is protruding from the guidewire. When the maximum curvature is above the threshold, the detection module 146 is configured to determine that the guidewire tip 111 is protruding the catheter 104. The determined maximum curvature of the FORS™ guidewire tip 111 in the default position may be utilized to normalize the measured curvature.

The detection module 146 is configured to send feedback to the user concerning the state of the catheter 104 and FORS™ guidewire 106. The feedback may be provided by a graphic generated on the display 109 or by other feedback known in the art including audio signals or haptic feedback. For example, the feedback provided by the detection module 146 concerning the state of the FORS™ guidewire 106 and catheter 104 may be useful for registration, such as shape to x-ray or shape to shape registration where it is preferable that the registration procedure be performed when the guidewire protrudes from the catheter.

The state of the guidewire 106 and catheter 104 may also be utilized to determine the length of the catheter. The user may position the guidewire 106 so that it protrudes from the catheter 104 and then retracts the guidewire so that the guidewire tip 111 is initially aligned with the catheter tip 117 and the guidewire tip is then moved within the catheter. The detection module 146 is configured to receive the 3D shape position of the guidewire at the aligned state and estimate the catheter length using a learned model.

Figure 22:
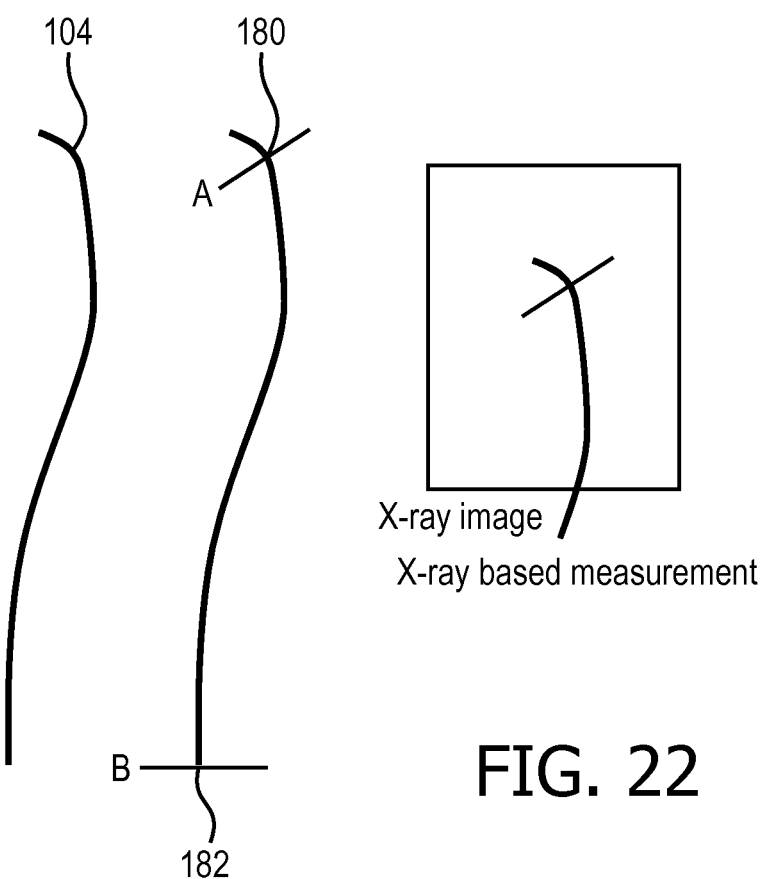
FIG. 22 is an image of a system which utilizes curvature data and the X-ray based length measurement to determine the total length of the interventional device.

In an alternative embodiment shown in FIG. 22, the curvature data from the FORS™ guidewire 106 is used to determine the catheter length from the start of the catheter to the position where the maximum curvature is exhibited. The imaging system 116, such as an x-ray imaging device, is utilized to measure the length of the remaining portion of the catheter. For example, in FIG. 22, the length of the catheter 104 between points 180 and 182 is measured by the FORS™ guidewire 106 in a manner previously discussed. The most distal portion of the catheter tip 117 is measured by identifying the points in an x-ray image.

Figure 23:
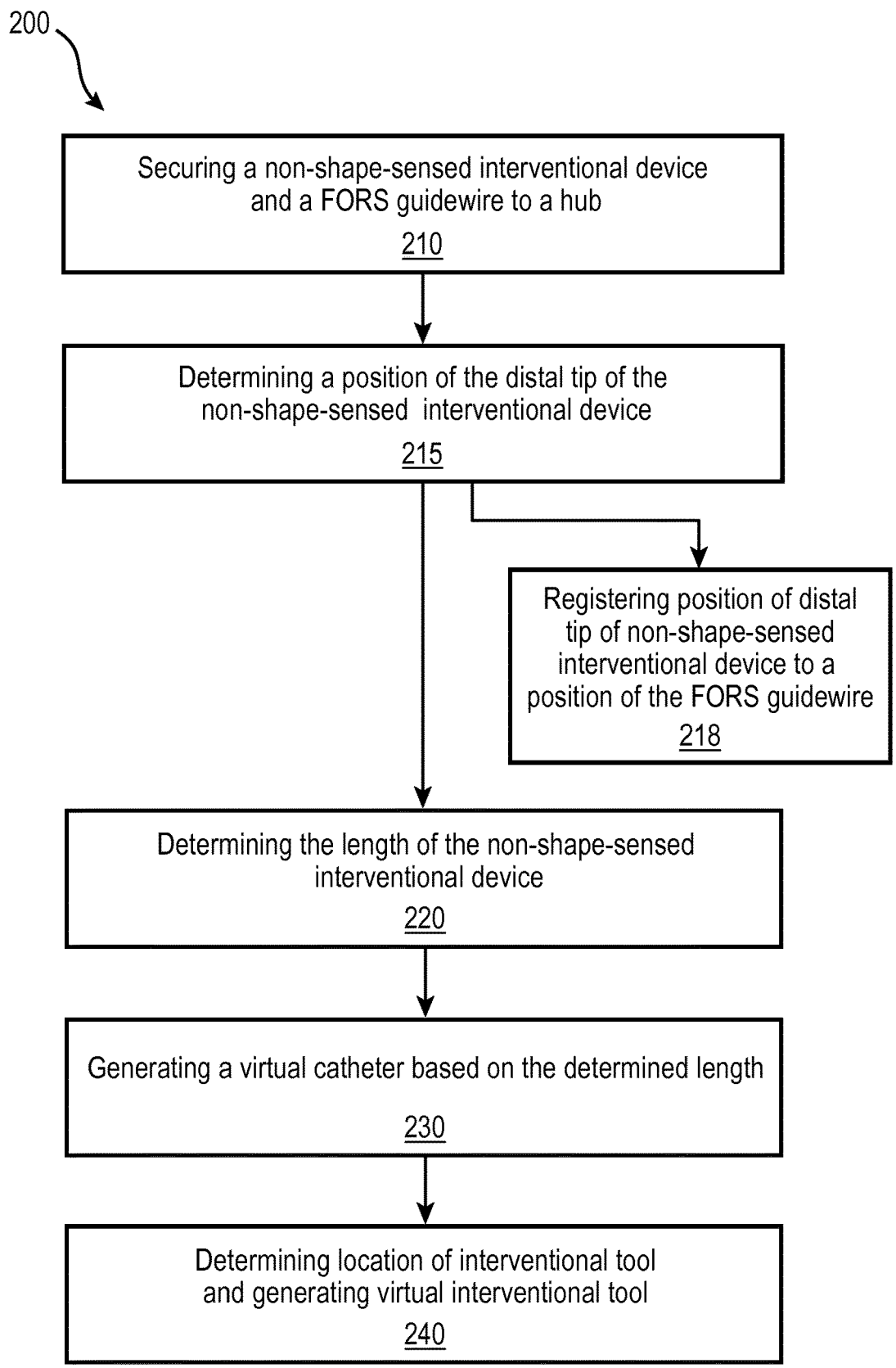
FIG. 23 is a flow diagram showing a method for determining the length of a non-shape-sensed interventional device.

Referring to FIG. 23, methods 200 for determining the length of a non-shape-sensed interventional device 102, such as a catheter 104, are illustratively shown in accordance with the present principles. In block 210, the non-shape-sensed interventional device and the FORS™ guidewire are secured to a hub having a lumen. The FORS™ guidewire is received in the lumen of the non-shape-sensed interventional device.

In block 215, a position of the distal tip of the non-shape-sensed interventional device is determined. The angle of rotation of the non-shape-sensed interventional device may also be determined based on measuring the rotation of the hub or the rotation of the distal tip of the catheter. The determination of the position of the distal tip of the non-shape-sensed interventional device preferably also involves the registration 218 of the position of the distal tip of the non-shape-sensed interventional device to a position of the FORS™ guidewire. As previously explained, the registration of the non-shape-sensed interventional device may include a manual or automatic selection of the positions of the tip of the FORS™ guidewire and the catheter from a plurality of different angles utilizing an imaging system, such as an x-ray imaging device. Alternatively, the catheter tip and the FORS™ guidewire tip may be aligned while the devices are locked to a hub to perform the registration. The known position of the hub and the aligned tips are utilized to register the positions of the proximal and distal end of the catheter.

In another embodiment, the FORS™ guidewire and the catheter may be secured to a hub at a proximal end and the tips are secured to a tip hub to register the positions of the proximal and distal tip of the catheter. In a further embodiment, the distal tip of the catheter is received by a fixture. The catheter and the FORS™ guidewire are received by a hub and the distal tip of the catheter is looped back onto the fixture from the hub to register the distal tip of the catheter.

In another embodiment, the FORS™ guidewire and catheter extend from the hub. The tip of the catheter is positioned at the body insertion point and the FORS™ guidewire extends into the body of the subject. The FORS™ guidewire is configured to measure temperature-induced strain to determine the transition point between the interior and exterior of the subject. The hub represents the beginning point of the catheter and the transition point represents the distal tip of the catheter.

Alternatively, the position of the distal tip of the catheter may be determined without an explicit registration step. For example, the difference between the length of a catheter visualized by an imaging system and a predetermined length may be determined and the actual length may be adjusted. In another embodiment, an imaging system is configured to image the entire non-shape-sensed device, such as the catheter, in a field of view and determine the length of the catheter.

In block 220, the length of the catheter is determined using the known position of the non-shape-sensed interventional device in the hub and the position of the distal tip of the non-shape-sensed interventional device.

In block 230, a virtual catheter is generated based on the determined length.

In block 240, the location of the interventional tool positioned along the non-shape-sensed device may also be determined as previously described utilizing radiopaque markers and an x-ray imaging registration procedure. A virtual representation of the interventional tool may be generated.

Figure 24:
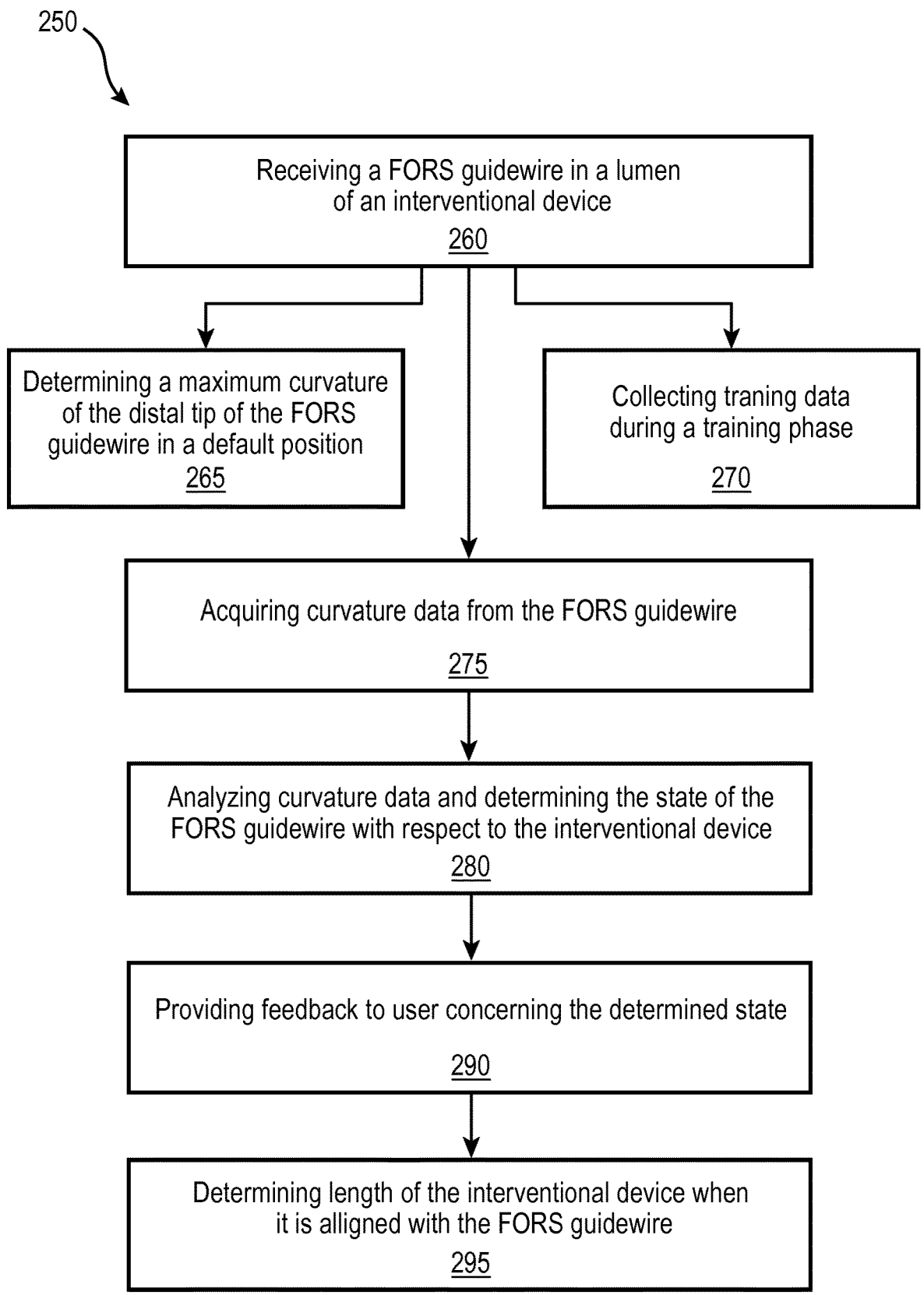
FIG. 24 is a flow diagram showing a method for determining the state of a FORS™ guidewire with respect to an interventional device.

Referring to FIG. 24, methods 250 for determining the state of a FORS™ guidewire with respect to a catheter (either a FORS™ catheter or non-shape-sensed catheter) are illustratively shown in accordance with the present principles. In block 260, the FORS™ guidewire having a shape sensing system is received in a lumen of an interventional device. In block 265, a maximum curvature of the FORS™ guidewire tip in a default position may be determined. In block 270, the guidewire and catheter may be manipulated in a sufficient number of positions during a training phase and training data is collected.

In block 275, curvature data for the FORS™ guidewire is acquired from the FORS™ shape sensing system. As previously described, the curvature data may be in the form of a graph. In block 280, the curvature data is analyzed and the state of the FORS™ guidewire with respect to the interventional device is determined. For example, the curvature data may be analyzed with respect to the training data to determine the state of the FORS™ guidewire and catheter. In block 290, feedback is provided to the user concerning the state of the FORS™ guidewire and catheter. In block 295, the length of the catheter may be determined by the 3D shape position of the guidewire when it is aligned with the FORS™ guidewire.

Figure 25A:
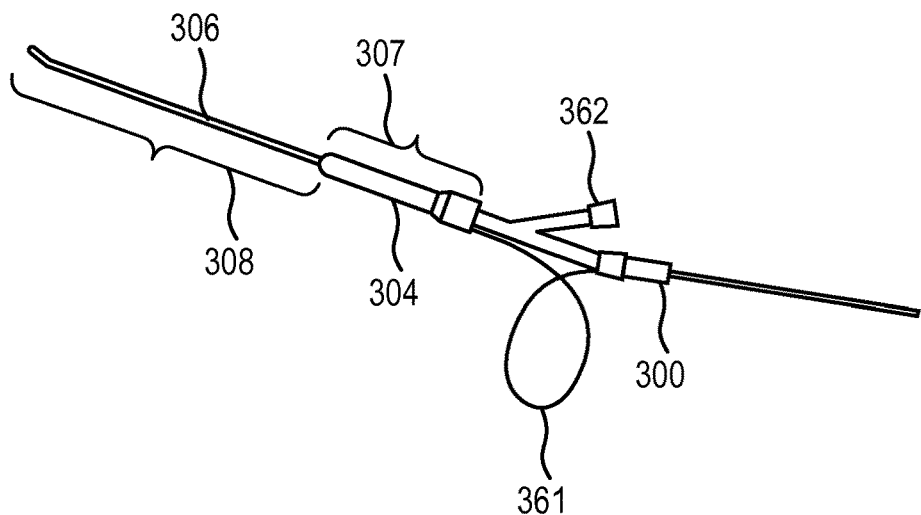
FIG. 25 shows an image of a guidewire with a torquer and string.
Figure 25B:
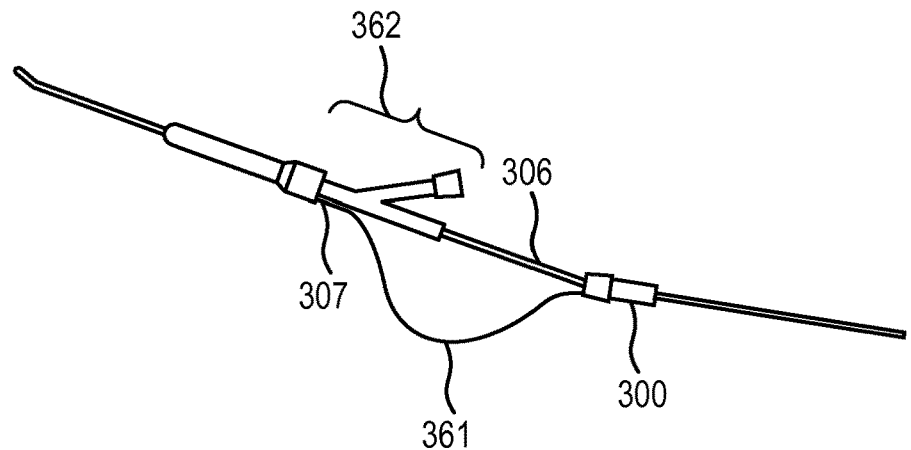
Figure 25C:
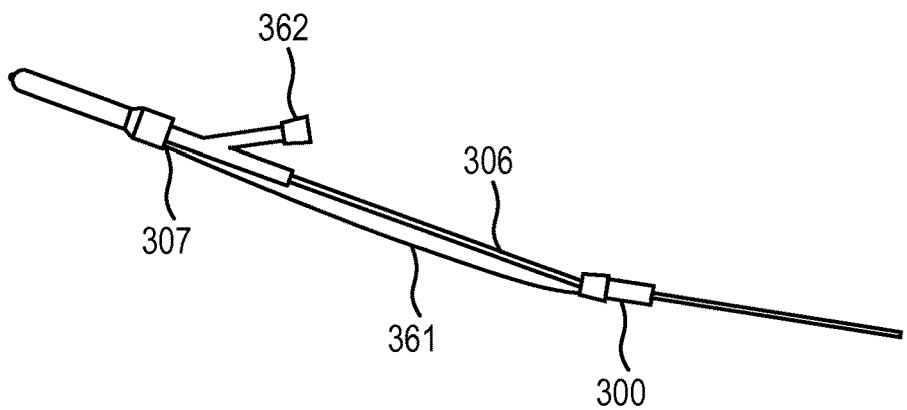

Referring to FIG. 25, a variable mechanical connection 361 is shown between a fixation point (a "torquer" 300) (which may be a hub or be located proximally from a hub and catheter (shown here together as 307) on a FORS-tracked guidewire 306 and non-shape sensed interventional device such as a catheter 304. The variable mechanical connection may be in the form of a string 361 or rod or concertina shape tubing or braiding (coaxially around the guide wire). The torquer 300 is positioned and clamped at a suitable position on the guide wire 306, the string 361 or other variable mechanical connector is attached to the torquer 300 with a length such that the end of the catheter 304 and the tip of the guide wire coincide (as shown by the stretched string 361 in FIG. 25C). The catheter 304 is then free to slide over a length 308 (the swing) of guide wire 306 as shown in FIG. 25A). The position of the torquer 300 and length of string 361 used may be adjusted to optimize the maximum swing. A hemostatic valve 362 in FIG. 25A-C serves as an endpoint for sliding motion of the torquer 300.

Registration of the tip of one device with respect to another is described above.

A spool may be provided, into which the string or other variable mechanical connection may be retracted. The spool may be configured to keep track of the length of the variable mechanical connection that is deployed or the length wrapped on the spool.

Very elastic tubing may be provided around a guide wire and/or braiding to keep the guidewire and variable mechanical connection together and to prevent the formation of knots or loops in the guidewire and variable mechanical connection that may catch on other parts during use.

An elastically bendable rod may connect a torquer and hub, the rod having a sliding end stop.

A quick release mechanism such as a spring, camlock, detent or lever may be provided on the torquer or hub to detach the string or other variable mechanical connection.

As explained above with respect to detection module 146, the detection module 146 may indicate during an intervention that the guidewire tip is inside the catheter or that the catheter tip and the guidewire tip are aligned. The determination of one of these states by the detection module 146 is advantageous for determining whether shape registration should be performed and the appropriate image processing procedure for such registration. Then, in addition or alternatively to the torquer and variable mechanical connection's mechanically preventing the guidewire from retracting and being unable to detect the shape and position of a part of the catheter, a visual and/or haptic warning may be provided to the physician that he or she has gone beyond an appropriate operating parameter. The warning may be a buzzer or light blinking. The warning may also be generated solely based on a detected maximum extension of the variable mechanical connection.

Some materials that could realistically be used for string or braiding are those with high young's modulus, such as Kevlar and Twaron, as shown in the following Table:

| Fibre | Characteristics | Modulus* (GPa) | Tensile Strength (GPa) | Extension to break (%) | Relative density (g/cm$^3$) |
|---|---|---|---|---|---|
| Nomex | | 17 | 0.6 | 22 | 1.38 |
| Fibre B | | 128 | 2.8 | 5 | 1.45 |
| Kevlar 29 | Regular | 70 | 2.9 | 4 | 1.44 |
| Kevlar 49 | High modulus | 135 | 2.9 | 2.8 | 1.45 |
| Kevlar 129 | High strength | 99 | 3.4 | 3.3 | 1.45 |
| Kevlar 149 | Ultra high modulus | 143 | 2.3 | 1.5 | 1.47 |
| Twaron | Regular | 79 | 3 | 3.3 | 1.44 |
| Twaron HM | High modulus | 123 | 2.8 | 2 | 1.44 |
| Technora | Regular | 70 | 3.3 | 4.3 | 1.39 |

Other materials may be chosen from among the Liquid Crystal Polymers (LCPs) which are thermoplastic resins that exhibit unique, exceptional mechanical strength, heat tolerance for autoclaving, and chemical inertness. These materials are used for, among other things catheter braiding. The young's modulus is 1-4 GPa.

Figure 26A:
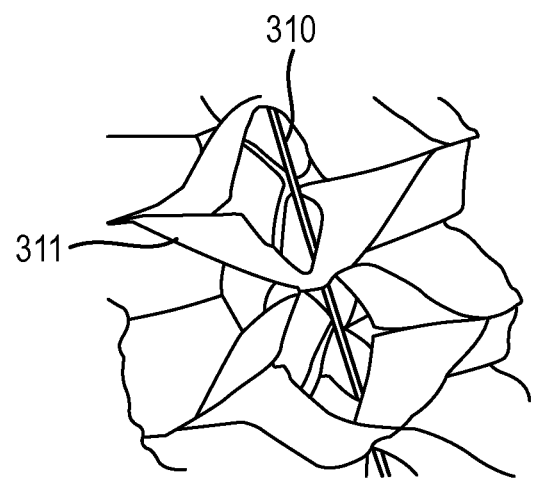
FIG. 26 shows shapes that are suitable for a variable mechanical connector.
Figure 26B:
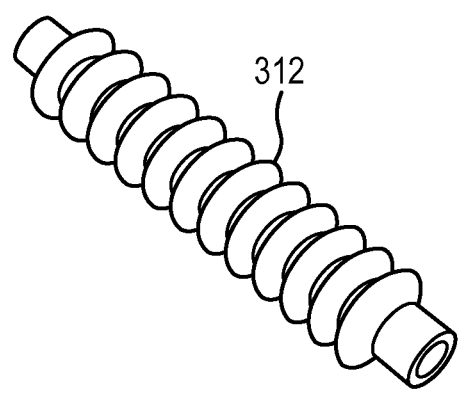

Some common shapes that may be used for the variable mechanical connection, instead of or in addition to, a string, are a shape like a concertina paper decoration 311 with central wire 310 as shown in FIG. 26A or a rubber bellows shape 312 as shown in FIG. 26B. Shape and material properties taken into account when specifying the variable mechanical connection may include: (1) short (flat) when folded/compressed, (2) long when expanded/deployed, (3) very little force required to go between the folded and expanded state (not elastic), and (4) when completely expanded the force required to expand further should abruptly become very high.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for a system for determining the length of a non-shape-sensed interventional device with a shape sensed guidewire and for determining a state of the guidewire with respect to an interventional device (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for determining length of a non-shape-sensed interventional device, comprising:
a non-shape-sensed interventional device having a lumen;
a shape-sensed guidewire having a shape sensing system that is configured to be received in the lumen of the non-shape-sensed interventional device;
a hub configured to receive the shape-sensed guidewire and the non-shape-sensed interventional device and fix a known position of the shape-sensed guidewire and the non-shape-sensed interventional device;
a registration module configured to register a position of a distal tip of the non-shape-sensed interventional device to a position of the shape-sensed guidewire as determined by the shape sensing system, to identify the position of the distal tip of the non-shape-sensed interventional device; and
a determination module configured to determine the length of the non-shape-sensed interventional device using the known position of the non-shape-sensed interventional device in the hub and the identified position of the distal tip of the non-shape-sensed interventional device.

2. The system as recited in claim 1, wherein the non-shape-sensed interventional device comprises a catheter.

3. The system as recited in claim 1,
further comprising an image processing module that is configured to generate a virtual image of the non-shape-sensed interventional device based on the length determined by the determination module.

4. The system as recited in claim 1, further comprising an imaging system;
wherein the imaging system is configured to acquire a plurality of images of the shape-sensed guidewire and the non-shape-sensed interventional device from different angles; and wherein the registration module is configured to receive a plurality of selected positions of a distal tip of the shape-sensed guidewire and the distal tip of the non-shape-sensed interventional device on the plurality of images, and to perform a transformation of the positions of the distal tip of the shape-sensed guidewire and the distal tip of the non-shape-sensed interventional device in a coordinate system of the imaging system to register the position of the distal tip of the non-shape-sensed interventional device to the position of the distal tip of the shape-sensed guidewire.

5. The system as recited in claim 4, further comprising:
an interventional tool positioned along a portion of the non-shape-sensed interventional device, wherein the registration module is configured to receive a plurality of selected positions of the interventional tool on the plurality of images, and to perform a transformation of the positions in the coordinate system of the imaging system to register a position of the interventional tool; and
an image processing module configured to generate a virtual image of the non-shape-sensed interventional device and a virtual image of the interventional tool.

6. The system as recited in claim 1, wherein the registration module is configured to register the position of the distal tip of the non-shape-sensed interventional device by determining a position of a distal tip of the shape-sensed guidewire when it is aligned with the distal tip of the non-shape-sensed interventional device.

7. The system as recited in claim 1, further comprising:
a tip hub configured to receive the distal tip of the non-shape-sensed interventional device and a distal tip of the shape-sensed guidewire,
wherein the registration module is configured to register the position of the distal tip of the non-shape-sensed interventional device using a known position of the tip hub.

8. The system as recited in claim 1, wherein the distal tip of the non-shape-sensed interventional device is looped back from the hub and is secured to a fixture having a known position; and
wherein the registration module is configured to register the position of the distal tip of the non-shape-sensed interventional device using the known position of the fixture.

9. A system for determining length of a non-shape-sensed interventional device, comprising:
a non-shape-sensed interventional device having a lumen;
a shape-sensed guidewire having a shape sensing system that is configured to be received in the lumen of the non-shape-sensed interventional device;
a hub configured to receive the shape-sensed guidewire and the non-shape-sensed interventional device and fix a known position of the shape-sensed guidewire and the non-shape-sensed interventional device;
a registration module configured to register a position of a distal tip of the non-shape-sensed interventional device to a position of the shape-sensed guidewire determined by the shape sensing system; and
a determination module configured to determine the length of the non-shape-sensed interventional device using the known position of the non-shape-sensed interventional device in the hub and the position of the distal tip of the non-shape-sensed interventional device, wherein the distal tip of the non-shape-sensed interventional device is looped back from the hub and contacts the shape-sensed guidewire; and wherein the registration module is further configured to identify a closest two points to register the position of the distal tip of the non-shape-sensed interventional device.

10. The system as recited in claim 1, wherein:
the registration module is configured to register an initial angle of rotation of the hub; and
the determination module is configured to compare a current angle of rotation of the hub with the initial angle of rotation of the hub to determine a shape and orientation of the distal tip of the non-shape-sensed interventional device.

11. A system for determining length of a non-shape-sensed interventional device, comprising:
a non-shape-sensed interventional device having a lumen;
a shape-sensed guidewire having a shape sensing system that is configured to be received in the lumen of the non-shape-sensed interventional device;
a hub configured to receive the shape-sensed guidewire and the non-shape-sensed interventional device and fix a known position of the shape-sensed guidewire and the non-shape-sensed interventional device; and
a determination module configured to determine the length of the non-shape-sensed interventional device using the known position of the non-shape-sensed interventional device in the hub and a position of a distal tip of the non-shape-sensed interventional device identified by registering a distal tip of the non-shape-sensed interventional device to the shape-sensed guidewire.

12. A method for determining length of a non-shape-sensed interventional device, the method comprising:
securing to a hub a non-shape-sensed interventional device having a lumen and a shape-sensed guidewire having a shape sensing system that is received in the lumen of the non-shape-sensed interventional device to secure a known position of the shape-sensed guidewire and the non-shape-sensed interventional device;
determining a position of a distal tip of the non-shape-sensed interventional device based on registering a distal tip of the non-shape-sensed interventional device to the shape-sensed guidewire; and
determining the length of the non-shape-sensed interventional device using the known position of the non-shape-sensed interventional device in the hub and the determined position of the distal tip of the non-shape-sensed interventional device.

13. The method as recited in claim 12, wherein the non-shape-sensed interventional device comprises a catheter.

14. The method as recited in claim 12, further comprising:
generating a virtual image of the non-shape-sensed interventional device based on the length determined by the determination module.

15. The method as recited in claim 12, wherein registering the distal tip of the non-shape-sensed interventional device to the shape-sensed guidewire comprises determining a position of a distal tip of the shape-sensed guidewire when it is aligned with the distal tip of the non-shape-sensed interventional device.

16. The method as recited in claim 12, further comprising:
looping back the distal tip of the non-shape-sensed interventional device from the hub and securing to a fixture having a known position, wherein the distal tip of the non-shape-sensed interventional device is registered using the known position of the fixture.

17. The method as recited in claim 12, further comprising:
looping back the distal tip of the non-shape-sensed interventional device from the hub and contacting the shape-sensed guidewire, wherein the distal tip of the non-shape-sensed interventional device is registered by identifying a closest two points to register a position of the distal tip of the non-shape-sensed interventional device.

\* \* \* \* \*